United States Patent
Karasawa et al.

(10) Patent No.: US 11,998,187 B2
(45) Date of Patent: Jun. 4, 2024

(54) SUTURE METHOD

(71) Applicants: OLYMPUS CORPORATION, Hachioji (JP); NATIONAL CANCER CENTER, Tokyo (JP)

(72) Inventors: Chisato Karasawa, Tokyo (JP); Satoru Nonaka, Tokyo (JP); Ichiro Oda, Tokyo (JP)

(73) Assignees: OLYMPUS CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 148 days.

(21) Appl. No.: 17/472,164

(22) Filed: Sep. 10, 2021

(65) Prior Publication Data

US 2023/0082982 A1    Mar. 16, 2023

(51) Int. Cl.
  *A61B 17/04*    (2006.01)
  *A61B 17/00*    (2006.01)
  *A61B 17/06*    (2006.01)

(52) U.S. Cl.
  CPC ...... *A61B 17/0469* (2013.01); *A61B 17/0487* (2013.01); *A61B 2017/00818* (2013.01); *A61B 2017/06052* (2013.01)

(58) Field of Classification Search
  CPC . A61B 17/04; A61B 17/0469; A61B 17/0487; A61B 2017/00818;
  (Continued)

(56) References Cited

U.S. PATENT DOCUMENTS

| | | | | |
|---|---|---|---|---|
| 4,162,678 A | * | 7/1979 | Fedotov | A61B 17/0682 227/176.1 |
| 4,955,897 A | * | 9/1990 | Ship | A61B 17/30 294/99.2 |

(Continued)

FOREIGN PATENT DOCUMENTS

| | | | | |
|---|---|---|---|---|
| CN | 109394309 A | * | 3/2019 | ........... A61B 17/285 |
| JP | 2010-036024 A | | 2/2010 | |

OTHER PUBLICATIONS

Schmidt A et al. Endoscopic full-thickness resection: Current status. World J Gastroenterol. Aug. 21, 2015;21(31):9273-85. doi: 10.3748/wjg.v21.i31.9273. PMID: 26309354; PMCID: PMC4541380. 14 pages. (Year: 2015).*

(Continued)

*Primary Examiner* — Julian W Woo
*Assistant Examiner* — Osama Nemer
(74) *Attorney, Agent, or Firm* — Oliff PLC

(57) ABSTRACT

A suture method includes a first arrangement step of using a first treatment device including first/second grasping pieces to hook the first grasping piece to a first position of peripheral tissues of a lesion; a second arrangement step of hooking the second grasping piece to a second position of the peripheral tissues; a grasping step of grasping the first position and the second position while pressing the first position and the second position to the peripheral tissues; a retracting step of retracting the lesion site toward a proximal end side of the first treatment device while drawing the first position and the second position grasped by the first treatment device; and a suturing step of suturing a first suturing position at an external side of the first position and a second suturing position at an external side of the second position in the peripheral tissues.

10 Claims, 27 Drawing Sheets

(58) Field of Classification Search
CPC .... A61B 2017/008; A61B 2017/00349; A61B 2017/00353; A61B 2017/00358; A61B 17/0057
See application file for complete search history.

(56) References Cited

U.S. PATENT DOCUMENTS

| | | | | |
|---|---|---|---|---|
| 5,292,326 | A * | 3/1994 | Green | A61B 17/04 227/181.1 |
| 6,352,503 | B1 * | 3/2002 | Matsui | A61B 1/00147 600/106 |
| 6,524,234 | B2 * | 2/2003 | Ouchi | A61B 1/018 606/115 |
| 6,605,104 | B2 * | 8/2003 | Sato | A61B 17/29 294/99.2 |
| 6,808,491 | B2 * | 10/2004 | Kortenbach | A61B 10/06 600/153 |
| 6,991,602 | B2 * | 1/2006 | Nakazawa | A61B 1/015 600/101 |
| 7,326,221 | B2 * | 2/2008 | Sakamoto | A61B 17/1285 623/2.11 |
| 7,334,718 | B2 * | 2/2008 | McAlister | A61B 17/068 227/175.1 |
| 8,074,857 | B2 * | 12/2011 | Peterson | A61B 17/068 227/175.1 |
| 8,863,748 | B2 * | 10/2014 | Kuroda | A61B 17/0401 600/106 |
| 8,876,698 | B2 * | 11/2014 | Sakamoto | A61B 17/0401 600/114 |
| 9,463,039 | B2 * | 10/2016 | Kuroda | A61B 17/221 |
| 9,844,377 | B2 * | 12/2017 | Peterson | A61B 17/10 |
| 10,085,747 | B2 * | 10/2018 | Peterson | A61B 17/0682 |
| 10,786,240 | B2 * | 9/2020 | Motai | A61B 17/062 |
| 11,389,185 | B2 * | 7/2022 | Golden | A61B 17/00234 |
| 2003/0032961 | A1 * | 2/2003 | Pelo | A61F 2/3872 606/301 |
| 2004/0138682 | A1 * | 7/2004 | Onuki | A61B 17/0643 606/205 |
| 2005/0033312 | A1 * | 2/2005 | Suzuki | A61B 17/1285 606/110 |
| 2005/0119524 | A1 * | 6/2005 | Sekine | A61B 17/0482 600/114 |
| 2007/0157937 | A1 * | 7/2007 | Mikkaichi | A61B 90/39 128/898 |
| 2008/0194999 | A1 * | 8/2008 | Yamaha | A61B 17/320068 601/2 |
| 2008/0255427 | A1 * | 10/2008 | Satake | A61B 17/08 606/205 |
| 2015/0150634 | A1 * | 6/2015 | Isoda | A61N 1/0517 606/130 |
| 2019/0290325 | A1 * | 9/2019 | Goto | A61B 17/3478 |
| 2019/0374221 | A1 * | 12/2019 | Asfora | A61B 17/0487 |
| 2020/0000513 | A1 * | 1/2020 | Motai | A61B 17/00234 |
| 2020/0038011 | A1 * | 2/2020 | Motai | A61B 17/062 |
| 2020/0100649 | A1 * | 4/2020 | Inoue | A61B 1/00133 |
| 2021/0121055 | A1 * | 4/2021 | Motai | A61B 1/018 |
| 2021/0186594 | A1 * | 6/2021 | Tanigami | A61B 1/0638 |
| 2021/0186650 | A1 * | 6/2021 | Taya | A61B 18/082 |

OTHER PUBLICATIONS

Hajifathalian K et al. Full-thickness resection device (FTRD) for treatment of upper gastrointestinal tract lesions: the first international experience. Endosc Int Open. Oct. 2020;8(10):E1291-E1301. doi: 10.1055/a-1216-1439. Epub Sep. 22, 2020. PMID: 33015330; PMCID: PMC7508667. 11 pages. (Year: 2020).*

FTRD Marking Probe. Ovesco Endoscopy AG. https://ovesco.com/ftrd-system/ftrd-marking-probe/#/eluidde05b763_1_0. Apr. 19, 2021. 9 pages. (Year: 2021).*

* cited by examiner

SUTURE METHOD

TECHNICAL FIELD

Background

The present disclosure relates to a suture method for suturing the gastrointestinal tract or the like.

BACKGROUND ART

Recently, in the surgery for suturing the gastrointestinal tract or the like, a suture method using a suturing device such as a stapler or the like is performed. It is possible to make the surgery for suturing the gastrointestinal tract or the like to be easy and shorten the surgery period by using the appropriate suturing device.

In Japanese Unexamined Patent Application, First Publication No. 2010-036024, a suturing device used by being attached to an endoscope is disclosed. A surgeon may perform the procedures for performing the full-thickness resection with respect to a portion including the lesion site such as the gastrointestinal tract and suturing the gastrointestinal tract using the endoscope with the suturing device attached thereto.

SUMMARY

According to an aspect of the present disclosure, a suture method for suturing peripheral tissues of a lesion site includes a first arrangement step of hooking a first grasping piece of a first treatment device having the first grasping piece and a second grasping piece to a first position of the peripheral tissues; a second arrangement step of hooking the second grasping piece to a second position of the peripheral tissues; a grasping step of grasping the first position and the second position; a retraction step of retracting the lesion site toward a proximal end side of the first treatment device while drawing together the first position and the second position grasped by the first treatment device; and a suturing step of suturing a first suturing position at an external side of the first position of the peripheral tissues and a second suturing position at an external side of the second position of the peripheral tissues.

DETAILED DESCRIPTION

First Embodiment

Hereinafter, a first embodiment of the present disclosure will be described with reference to FIG. 1 to FIG. 15.

Figure 1:
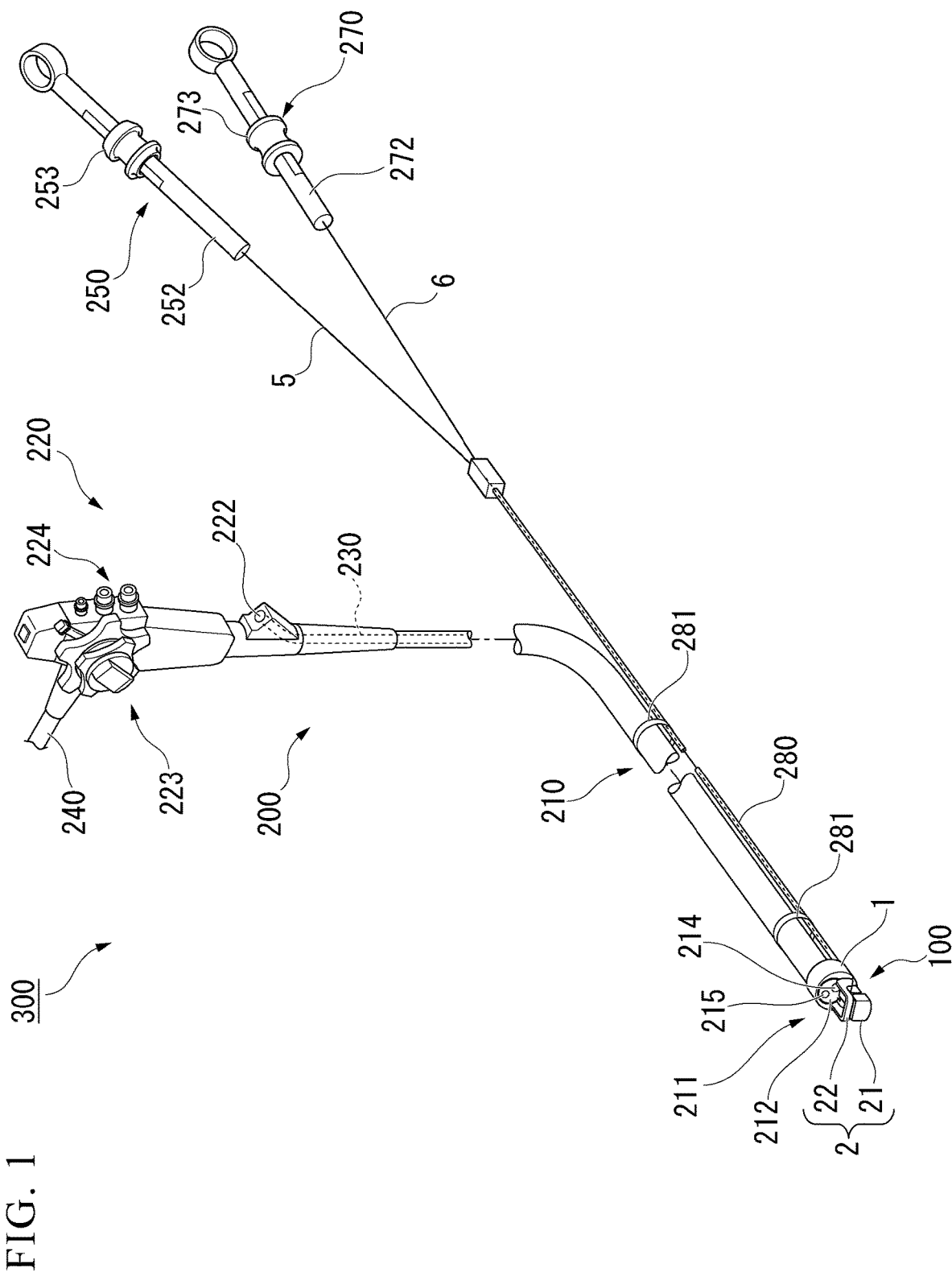
FIG. 1 is a schematic view showing a medical system used in a suture method according to a first embodiment of the present disclosure.

FIG. 1 is a view showing an overall configuration of a medical system 300 used in a suture method according to the present embodiment. The medical system used in the suture method according to the present embodiment is not limited to the medical system 300.

Medical System 300

The medical system 300 is used in a surgery for suturing the gastrointestinal tract or the like. The medical system 300 includes a medical stapler 100, an endoscope 200, an open-close operation portion 250, an extraction-operation portion 270, and a wire sheath 280. The open-close operation portion 250 is the operation portion configured to operate the medical stapler 100 via an open-close operation wire 5. The extraction-operation portion 270 is the operation portion configured to operate the medical stapler 100 via an extraction-operation wire 6.

Endoscope 200

The endoscope 200 is a conventional flexible endoscope, and the endoscope 200 includes an elongated insertion portion 210 to be inserted into the body from a distal end thereof, an operation portion 220 provided at a proximal end portion of the insertion portion 210, and a universal code 240.

A treatment device channel 230 configured for inserting through the endoscopic treatment device is formed in the insertion portion 210. A forceps port 214 as a distal opening of the treatment device channel 230 is formed in a distal end 212 of the insertion portion 210. The treatment device channel 230 extends from the distal end 212 of the insertion portion 210 until the operation portion 220.

An imaging unit (not shown) including a CCD or the like is provided in a distal end portion 212 of the insertion portion 210. The object lens 215 of the imaging unit is exposed at the distal end 212 of the insertion portion 210.

A knob 223 for operating the insertion portion 210 and a switch 224 for operating the imaging unit or the like are provided in the proximal end side of the operation portion 220. The surgeon may operate the knob 223 to direct the insertion portion 210 to a desired direction.

A forceps insertion port 222 communicating with the treatment device channel 230 is provided in the distal end side of the operation portion 220. The surgeon may insert the endoscopic treatment device from the forceps insertion port 222 into the treatment device channel 230.

The universal code 240 is configured to connect the operation portion 220 with external peripheral apparatus. The universal code 240, for example, is configured to output the images captured by the imaging unit to the external apparatus. The images captured by the imaging unit is processed by an image processing apparatus and displayed on a display apparatus such as a Liquid display or the like.

Open-Close Operation Portion 250

The open-close operation portion 250 is the operation portion to open and close the medical stapler 100 by operating the open-close operation wire 5. As shown in FIG. 1, the open-close operation portion 250 includes an open-close operation main body 252 and an open-close operation slider 253. The surgeon may advance or retract the open-close operation slider 253 in a longitudinal direction with respect to the open-close operation main body 252 so as to advance and retract the open-close operation wire 5.

Extraction-Operation Portion 270

The extraction-operation portion 270 is the operation portion for extracting (ejecting) a staple S from the medical stapler 100 by operating the extraction-operation wire 6. The extraction-operation portion 270, as shown in FIG. 1, includes an extraction-operation main body 272 and an extraction-operation slider 273. The distal end of the extraction-operation wire 6 is connected to the extraction-operation slider 273. The surgeon may advance and retract the extraction-operation wire 6 by advancing and retracting the extraction-operation slider 273 in the longitudinal direction with respect to the extraction-operation main body 272.

Wire Sheath 280

The wire sheath 280 is the sheath through which the open-close operation wire 5 and the extraction-operation wire 6 are inserted. As shown in FIG. 1, the distal end side of the wire sheath 280 is connected to the insertion portion 210 of the endoscope 200 by a band 281.

Medical Stapler 100

Figure 2:
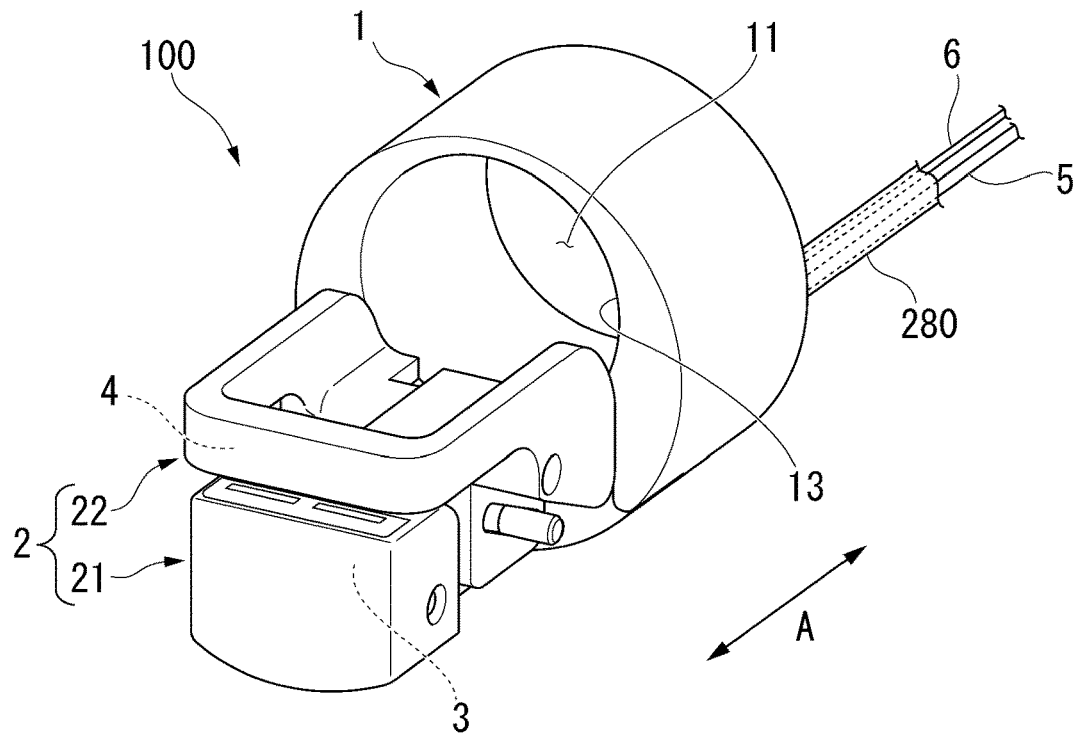
FIG. 2 is a perspective view showing a medical stapler.

FIG. 2 is a perspective view showing the medical stapler 100.

The medical stapler (suturing device) 100 includes a cap 1, a grasping portion 2, a staple extraction portion 3, a staple accommodation portion 4, the open-close operation wire 5, and the extraction-operation wire (force transmission member) 6. The medical stapler 100 is capable of being attached to or detached from the distal end portion 211 of the insertion portion 210.

Figure 3:
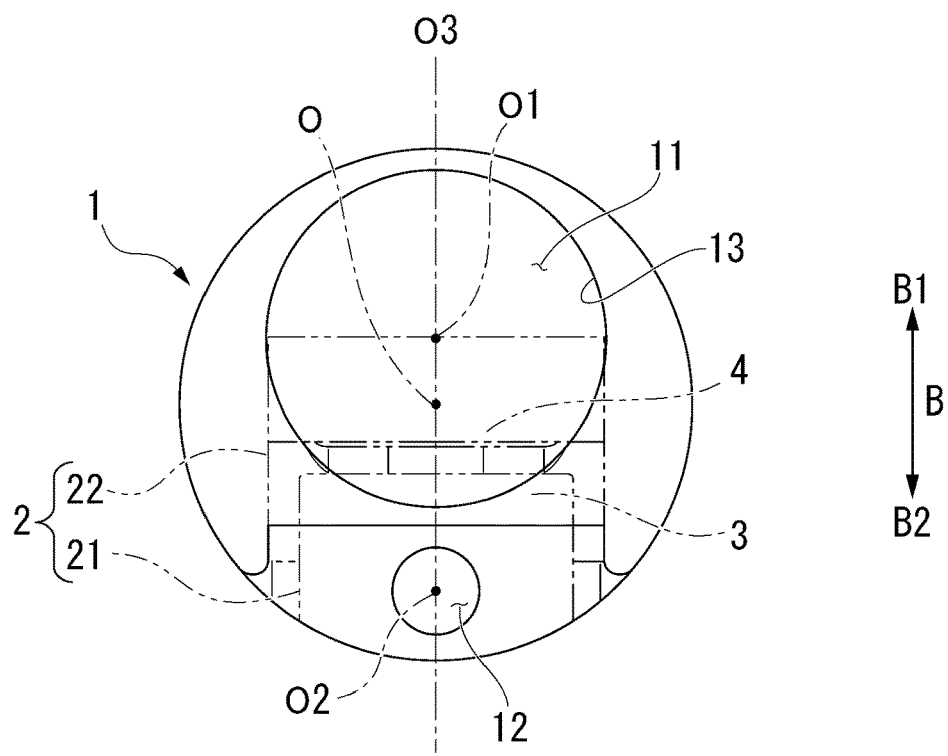
FIG. 3 is a front view showing a cap of the medical stapler.

FIG. 3 is a front view of the cap 1. In FIG. 3, the grasping portion 2 is transparently displayed.

The cap (attachment portion) 1 is the member capable of being attached to and detached from the distal end portion 211 of the endoscope 200. The cap 1 is formed in a substantially cylindrical shape, and the cap 1 includes a first penetration hole 11 penetrating along the axial direction A and a second penetration hole 12 penetrating along the axial direction A.

The first penetration hole 11 is the hole through which the distal end portion 211 of the insertion portion 210 of the endoscope 200 is inserted. The shape of the first penetration hole is formed following the outfit of the distal end portion 211 of the insertion portion 210. Accordingly, it is possible to attach the cap 1 to the distal end portion 211 of the endoscope 200 by inserting the distal end portion 211 of the endoscope 200 into the first penetration hole 11.

As shown in FIG. 3, a central axis O1 of the first penetration hole 11 along the axial direction A is eccentric with respect to the central axis O of the cap 1 along the axial direction A. A direction from the central axis O toward the eccentric central axis O1 is defined as an "upper direction B1".

The second penetration hole 12 is the hole into which the wire sheath 280 is inserted, wherein the open-close operation wire 5 and the extraction-operation wire 6 are inserted through the wire sheath 280. An inner diameter of the second penetration hole 12 is substantially the same with an outer diameter of the wire sheath 280. A distal end portion of the wire sheath 280 is inserted through the second penetration hole 12 and fixed. The open-close operation wire 5 and the extraction-operation wire 6 being inserted through the wire sheath 280 pass through the second penetration hole 12 so as to extend to the distal end side.

As shown in FIG. 3, a central axis O2 of the second penetration hole 12 along the axial direction A is eccentric with respect to the central axis O of the cap 1 along the axial direction A. A direction from the central axis O toward the eccentric central axis O2 is opposite to the direction (upper direction B1) from the central axis O toward the eccentric central axis O1. The direction from the central axis O toward the eccentric central axis O2 is defined as a "lower direction B2". In the present embodiment, the upper direction B1 and the lower direction B2 are along the vertical direction B.

Figure 4:
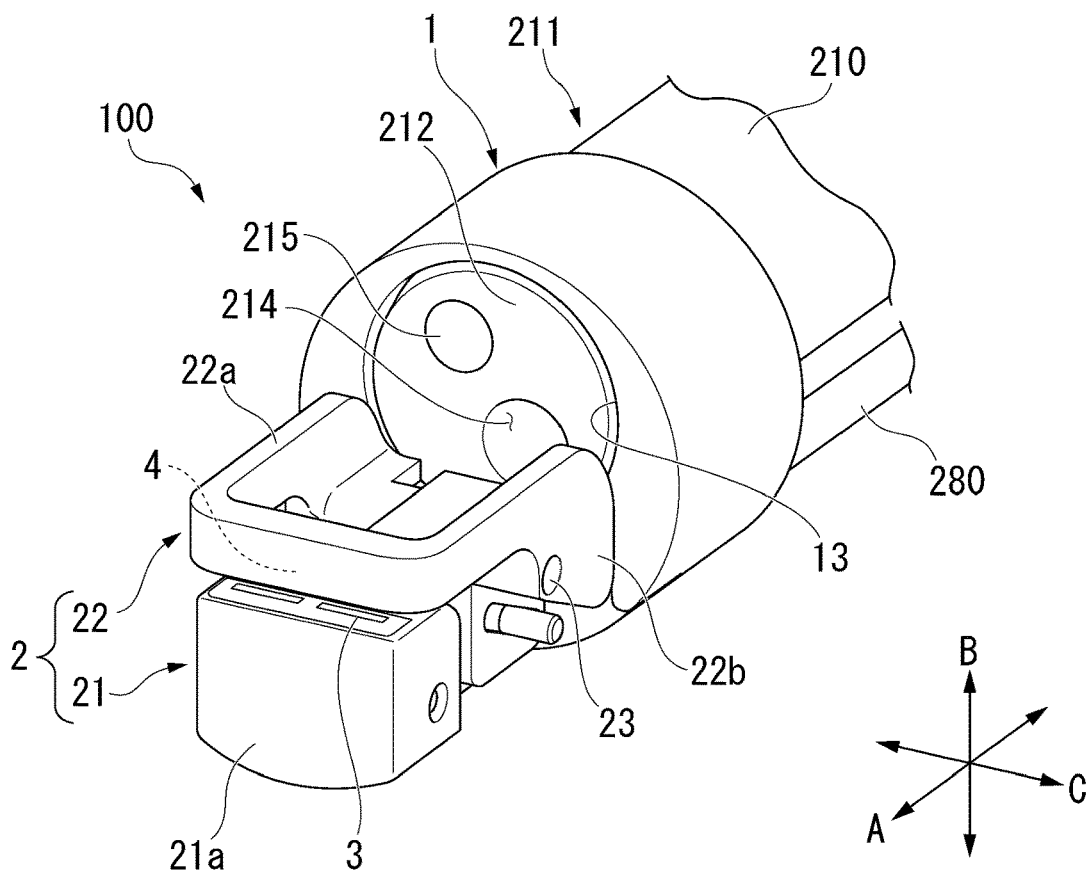
FIG. 4 is a perspective view of the medical stapler whose grasping portion is in a closed state.
Figure 5:
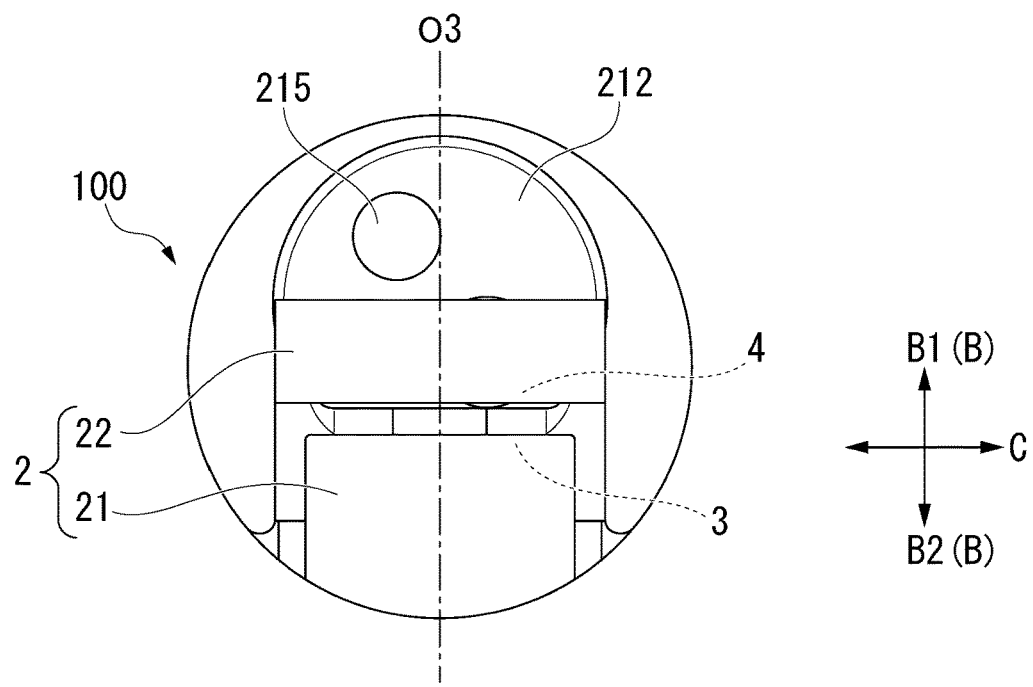
FIG. 5 is a front view of the medical stapler whose grasping portion is in the closed state.

FIG. 4 and FIG. 5 are the perspective view and the front view of the medical stapler 100 wherein the grasping portion 2 is in the closed state, respectively.

When the cap 1 is attached to the distal end portion 211 of the endoscope 200, as shown in FIG. 4 and FIG. 5, the object lens 215 and the forceps port 214 are exposed from the opening 13 at the distal end side of the first penetration hole 11 of the cap 1. The surgeon may observe the treatment target using the object lens 215 even in the state in which the medical stapler 100 is attached to the distal end portion 211 of the endoscope 200.

Figure 6:
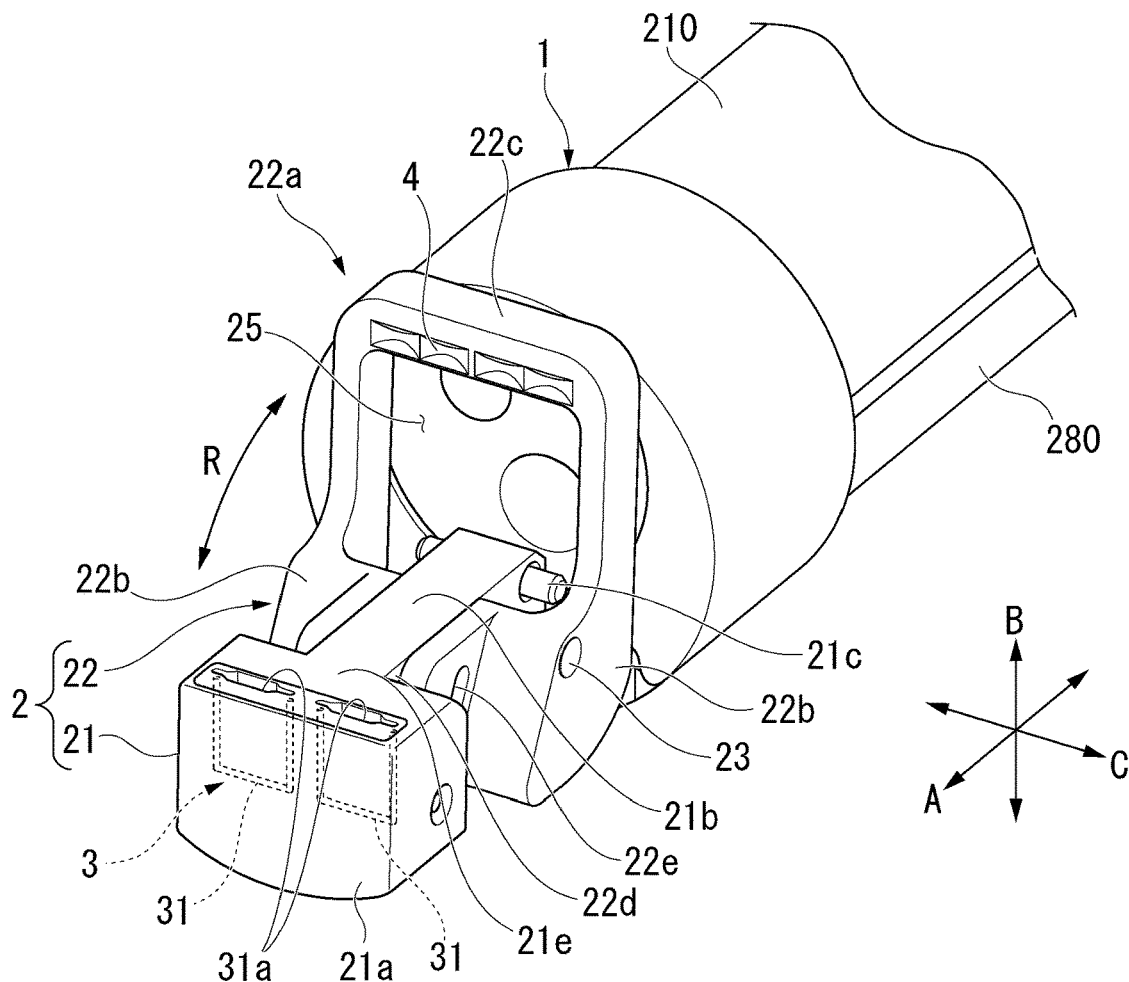
FIG. 6 is a perspective view of the medical stapler whose grasping portion is in an open state.
Figure 7:
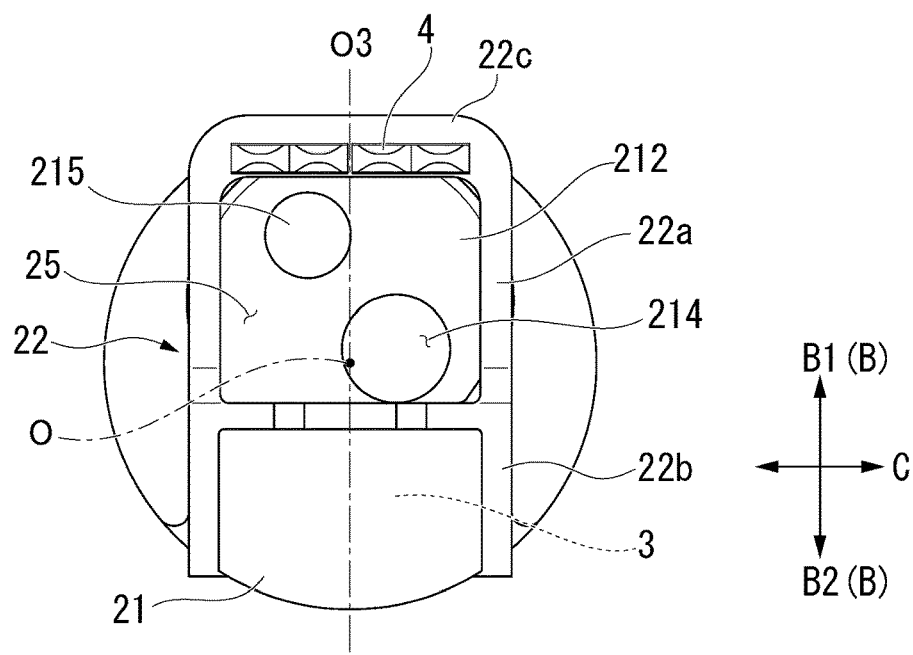
FIG. 7 is a front view of the medical stapler whose grasping portion is in the open state.
Figure 8:
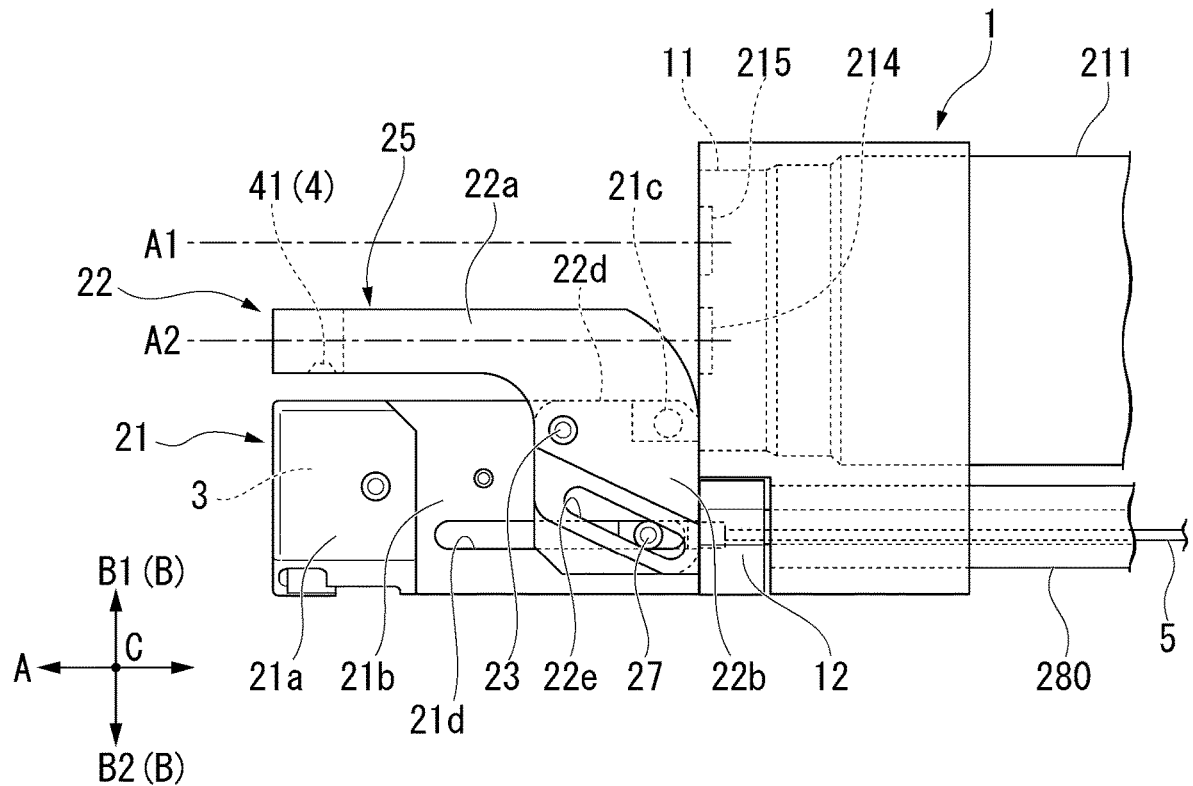
FIG. 8 is a side view of the medical stapler whose grasping portion is in the closed state.
Figure 9:
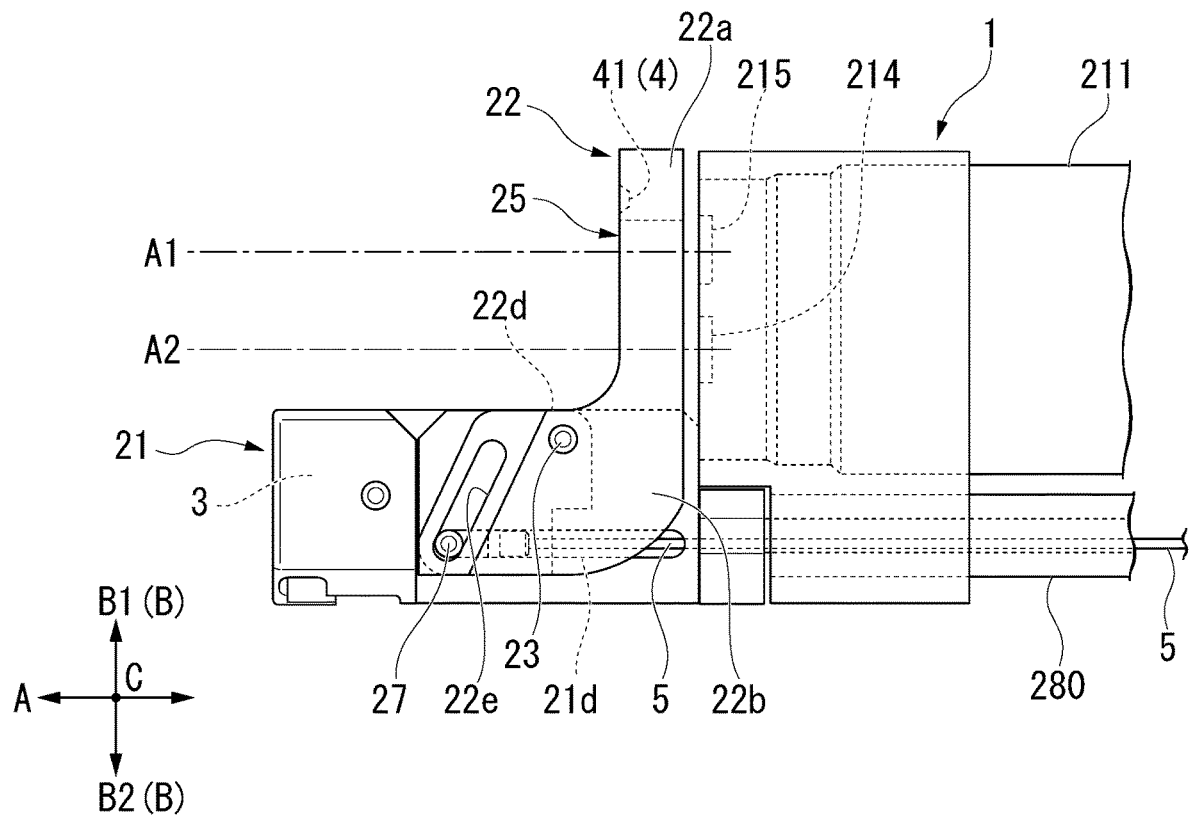
FIG. 9 is a side view of the medical stapler whose grasping portion is in the open state.

FIG. 6 and FIG. 7 are the perspective view and the front view of the medical stapler 100 wherein the grasping portion 2 is in the open state, respectively. Furthermore, FIG. 8 is the side view of the medical stapler 100 when the grasping portion 2 is in the closed state. FIG. 9 is the side view of the medical stapler 100 when the grasping portion 2 is in the open state.

As shown in FIG. 8, the grasping portion 2 includes a first grasping member 21, a second grasping member 22, an open-close rotation shaft 23, and a moveable pin 27. The first grasping member 21 and the second grasping member 22 are connected by the open-close rotation shaft 23 so as to be open and closed. The open-close rotation shaft 23 is provided at the distal end side of the cap 1. The axial direction C of the open-close rotation shaft 23 is orthogonal to the axial direction A of the cap 1 and the vertical direction B. As shown in FIG. 7, the grasping portion 2 is formed to be symmetrical with respect to the central axis O3 along the vertical direction B.

The first grasping member 21 is fixed to the distal end side of the cap 1 so as to be unable to rotate. The first grasping member 21 is fixed to the cap 1 at the lower direction B2 side with respect to the central axis O of the cap 1. As shown in FIG. 3, the first grasping member 21 is disposed at the position overlapping the second penetration hole 12 in the front view. On the other hand, as shown in FIG. 7, the first grasping member 21 is disposed at the position not to overlap the object lens 215 and the forceps port 214 of the endoscope 200 in the front view.

As shown in FIG. 6, the first grasping member 21 has a first distal end portion 21a and a first main body portion 21b, and the first grasping member 21 is formed in a substantial T shape in a planar view. The first distal end portion 21a is disposed at the distal end side of the first main body portion 21b.

The first distal end portion 21 is formed in a substantial rectangular cuboid shape. The first distal end portion 21a is formed in a rectangle shape extending along the axial direction C of the open-close rotation shaft 23 in the planar view. The staple extraction portion 3 is provided in the first distal end portion 21a. An opening 31a of the staple extraction portion 3 is formed in a surface (upper surface 21e) in the upper direction B1 of the first distal end portion 21a.

The first main body portion 21b is an elongated member extending along the axial direction A. The distal end of the first main body portion 21b is fixed to the first distal end portion 21a. The proximal end of the first main body portion 21b is fixed to the cap 1 via the wire sheath 280. The first main body portion 21b includes a contact pin 21c and a first engagement groove 21d (see FIG. 8).

The contact pin 21c is provided in the proximal end of the first main body portion 21b, the contact pin 21c is configured to come in contact with the second grasping member 22 in the closed state so as to restrict the movable range of the second grasping member 22.

As shown in FIG. 8, the first engagement groove 21d is the groove penetrating along the axial direction C of the open-close rotation shaft 23 in the first main body portion 21b. The first engagement groove 21d extends along the axial direction A.

The second grasping member 22 is attached to the first grasping member 21 by the open-close rotation shaft 23 to be rotatable. The second grasping member 22 includes a U-shaped member 22a formed in a substantial U shape and a second main body 22b configured to support the U-shaped member 22a such that the U-shaped member 22a is rotatable.

The U-shaped member 22a is formed in a substantial U shape, wherein two end portions are connected to the second main body portion 22b and the central portion is disposed at the distal end side. As shown in FIG. 7, the central portion includes the second distal end portion 22c. The second distal end portion 22c is formed in the substantial rectangular cuboid shape. The staple accommodation portion 4 is disposed in the second distal end portion 22c.

The second main body portion 22b is attached to the first main body portion 21b of the first grasping member 21 by the open-close rotation shaft 23 so as to be rotatable. Guide grooves 22d into which the first main body portion 21b is inserted are formed in the second main body portion 22b. Second engagement grooves 22e are formed in the two side portions of the guide grooves 22d of the second main body portion 22b.

The second engagement grooves 22e are formed in the second main body portion 22b. The second engagement grooves 22e are the grooves penetrating along the axial direction C. In the side view, the second engagement groove 22e is formed at the opposite side of the staple accommodation portion 4 to sandwich the open-close rotation shaft 23 therebetween. The second engagement groove 22e is symmetric with respect to the central axis O3 of the second grasping member 22.

As shown in FIG. 6, the second grasping member 22 has a view space 25 penetrating in the open-close direction R between the staple accommodation portion 4 at the distal end side and the open-close rotation shaft 23 at the proximal end side. In the present embodiment, the view space 25 is the space surrounding by the sides of the U-shaped member 22a formed in the substantial U shape.

As shown in FIG. 8, the movable pin 27 is engaged with the first engagement groove 21d and the second engagement groove 21e, and the movable pin 27 advances and retracts in the axial direction A along the first engagement groove 21d. The distal end of the open-close operation wire 5 is attached to the movable pin 27. As shown in FIG. 9, the open-close operation wire 5 advances toward the distal end side such that the movable pin 27 rotates the second grasping member 22 with the open-close rotation shaft 23 as the rotation center to make the grasping portion 2 into the open state. The open-close operation wire 5 retracts toward the proximal end side such that as shown in FIG. 8, the movable pin 27 rotates the second grasping member 22 with the open-close rotation shaft 23 as the rotation center to make the grasping portion 2 into the closed state.

As shown in FIG. 5, when the grasping portion 2 is in the closed state, the staple extraction portion 3 and the staple accommodation portion 4 are opposite to each other. When the grasping portion 2 is in the closed state, a slight gap is formed between the staple extraction portion 3 and the staple accommodation portion 4. As shown in FIG. 8, when the grasping portion 2 is in the closed state, an optical axis A1 of the object lens 215 passes through in the upper direction B1 of the first grasping member 21 and the second grasping member 22. When the grasping portion 2 is in the closed state, in the front view, the central axis A2 of the forceps port 214 does not overlap the first grasping member 21; however, the central axis A2 of the forceps port 214 is at the position overlapping the second grasping member 22.

As shown in FIG. 9, when the grasping portion 2 is in the open state, the staple accommodation portion 4 is disposed at the proximal end side of the open-close rotation shaft 23. When the grasping portion 2 is in the open state, the staple extraction portion 3 and the staple accommodation portion 4 are disposed in the upper direction B1 and the lower direction B2 respectively to sandwich the optical axis A1 of the object lens 215. When the grasping portion 2 is in the open state, the optical axis A1 of the object lens 215 passes through the view space 25. When the grasping portion 2 is in the open state, the central axis A2 of the forceps port 214 passes through the view space 25.

Figure 10:
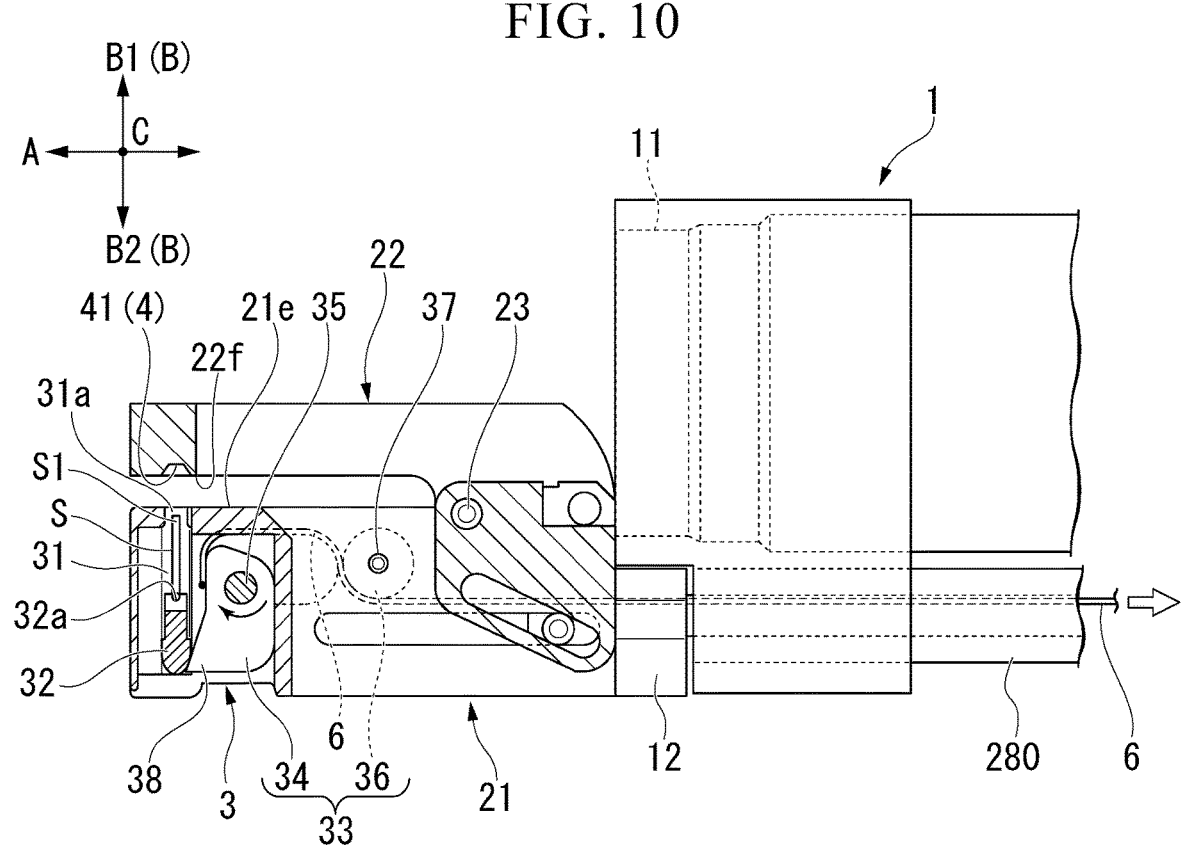
FIG. 10 is a cross-sectional view of the grasping portion including a staple extraction portion.

FIG. 10 is a cross-sectional view showing the grasping portion 2 including the staple extraction portion 3.

The staple extraction portion 3 is provided in the first distal end portion 21a of the first grasping member 21, and the staple extraction portion 3 is configured to accommodate and extract the staple S. The staple extraction portion 3 includes a staple accommodation portion 31, a rectilinear member 32, and a rotation member 33.

The staple accommodation portion 31 is a space provided in the first distal end portion 21a of the first grasping member 21 for accommodating the staple S. In the first grasping member 21, as shown in FIG. 6, two staple accommodation portions 31 are formed to be side by side in the axial direction C so as to be able to accommodate two U-shaped staples S.

The staple accommodation portion 31 opens in the vertical direction B in the opening 31a provided in the upper surface 21e of the first distal end portion 21a. The staple S is accommodated in the staple accommodation portion 31 from the opening 31a. The staple S is accommodated in the staple accommodation portion 31 in a state in which a needle tip S1 of the staple S is directed toward the upper direction B1.

In the planar view, the staple accommodation portion 31 is formed in a rectangle shape whose short side extends along the axial direction A and the long side extends along the axial direction C. The needle tips S1 at two ends of the staple S accommodated in the staple accommodation portion 31 are arrayed along the axial direction C.

The rectilinear member 32 is the member being accommodated by the staple accommodation portion 31, and the rectilinear member 32 is movable in the internal space of the staple accommodation portion 31 in the vertical direction B. The rectilinear member 32 includes a concave portion 32a in the upper direction B1 to support the staple S. The staple S accommodated in the staple accommodation portion 31 is fitted in the concave portion 32a.

A first pulley 34 and a second pulley 36 as the rotation member 33 are attached in the first grasping member 21 to be rotatable, and the first pulley 34 and the second pulley 36 rotate so as to move the rectilinear member 32 in the vertical direction B. The distal end of the extraction-operation wire 6 is connected to the pulley 34. It is possible to rotate the first pulley 34 by pulling the extraction-operation wire 6.

The second pulley 36 is attached in the first grasping member 21 to be rotatable, and the first pulley 34 is disposed at the distal end side than the second pulley 36. The rotation axis 35 of the first pulley 34 and the rotation axis 37 of the second pulley 36 extend along the axial direction C and substantially parallel to the open-close rotation shaft 23 of the grasping portion 2. The first pulley 34 includes a convex portion (contact portion) 38 at the distal end side thereof for supporting the rectilinear member 32 from the lower direction B2.

The distal end of the extraction-operation wire 6 is connected to the first pulley 34 in the upper direction B1 with respect to the rotation axis 35. The extraction-operation wire 6 passes through the second penetration hole 12 from the first pulley 34 via the second pulley 36 and extends to the extraction operation portion 270.

Figure 11:
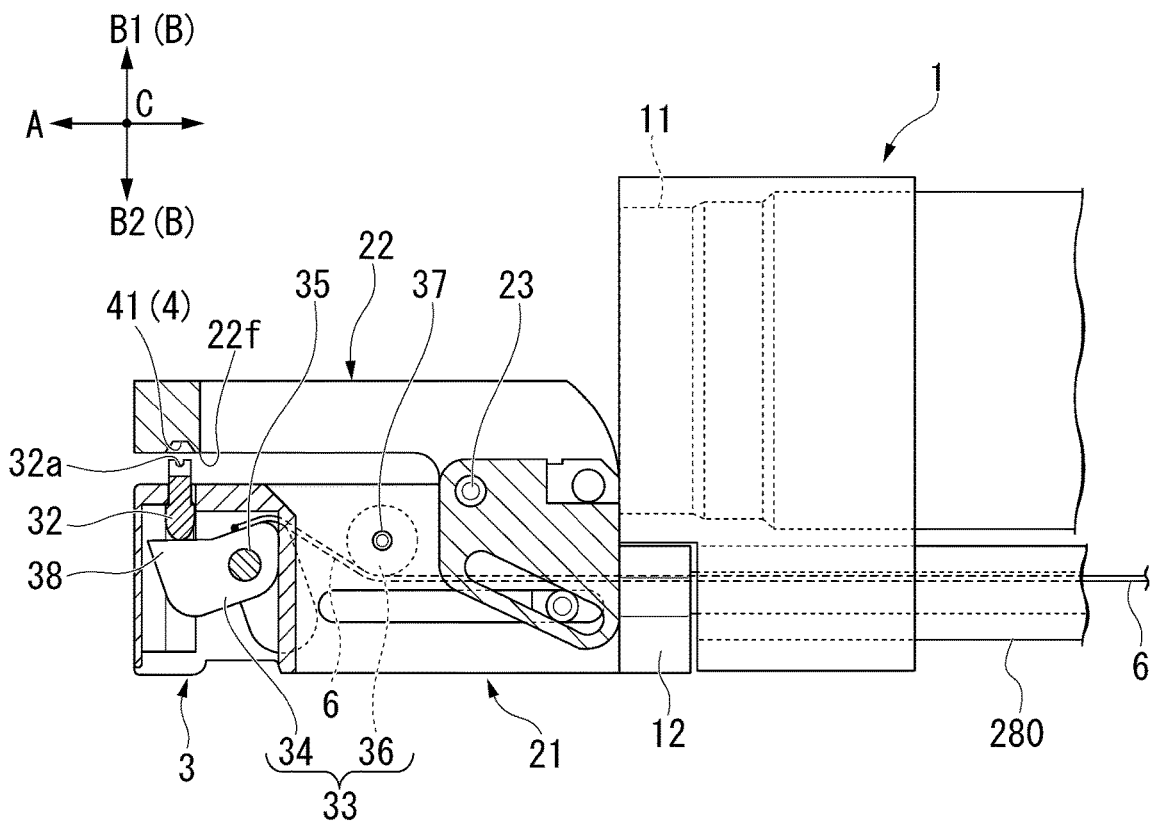
FIG. 11 is a cross-sectional view of the grasping portion when an extraction-operation wire is pulled.

FIG. 11 is a cross-sectional view showing the grasping portion 2 being pulled by the extraction-operation wire 6.

The extraction-operation wire 6 is pulled such that the first pulley 34 rotates and the convex portion 38 of the first pulley 34 pushes the rectilinear member 32 up in the upper direction B1 so as to extract the accommodated staple S from the opening 31a toward the upper direction B1.

The staple accommodation portion (anvil) 4 is disposed on the lower surface 22f of the second distal end portion 22c of the second grasping member 22. A plurality of pockets 41 capable of accommodating the staples S extracted from the staple extraction portion 3 are provided in the staple accommodation portion 4. In the present embodiment, since two of the U-shaped staples are extracted from the staple extraction portion 3, there are four pockets provided in the staple accommodation portion 4. When the grasping portion 2 is in the closed state, the opening 31a for extracting the staple S and the pocket 41 of the staple accommodation portion 4 are opposite to each other.

Usage of Medical Stapler 100

Next, the usage of the medical stapler 100 (suture method using the medical stapler 100) will be described. FIG. 12 to FIG. 18 are views showing the usage of the medical stapler 100.

Insertion Step

The surgeon or the assistant (hereinafter simply referred to as the surgeon) inserts the insertion portion 210 of the endoscope 200 to which the medical stapler 100 is attached from the mouth as the natural orifice and approaches the distal end portion 211 to the treatment target T. The surgeon operates the open-close operation portion 250 to advance the open-close operation wire 5 and make the grasping portion 2 into the open state.

When the grasping portion 2 is in the open state, as shown in FIG. 9, since the optical axis A1 passes through the view space 25, the surgeon may observe the treatment target T via the imaging unit of the endoscope 200.

Marking Step

Figure 12:
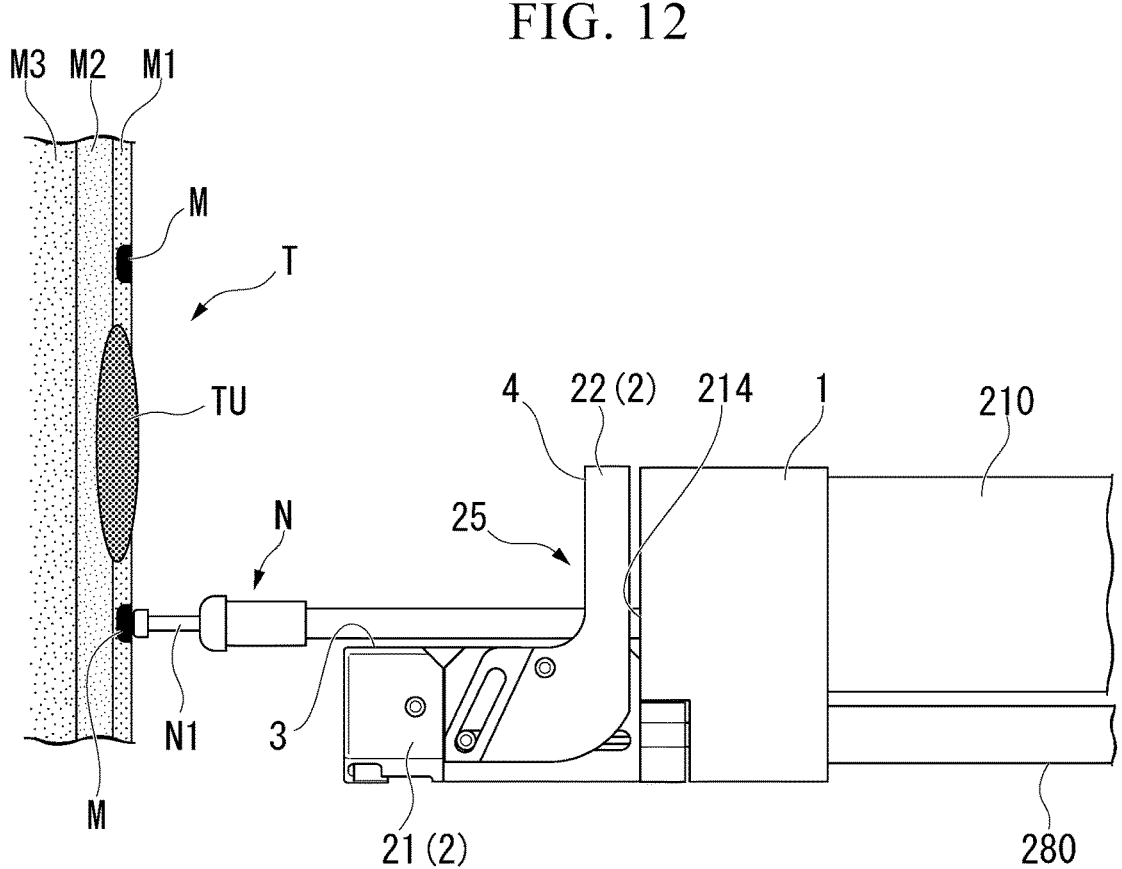
FIG. 12 is a view showing a marking step in the present suture method.

As shown in FIG. 12, the surgeon inserts the high-frequency knife N as the treatment device for marking (third treatment device) into the treatment device channel 230, and protrudes the knife N1 disposed at the distal end of the high-frequency knife N from the forceps port 214. Since the central axis A2 of the forceps port 214 passes through the view space 25, the knife N1 of the high-frequency knife N may pass through the grasping portion 2 to approach the treatment target T positioned at the distal end side. The treatment device for marking (third treatment device) may be high-frequency forceps, a high-frequency snare, a heating element such as a heat probe, or an ultrasonic device.

Figure 13:
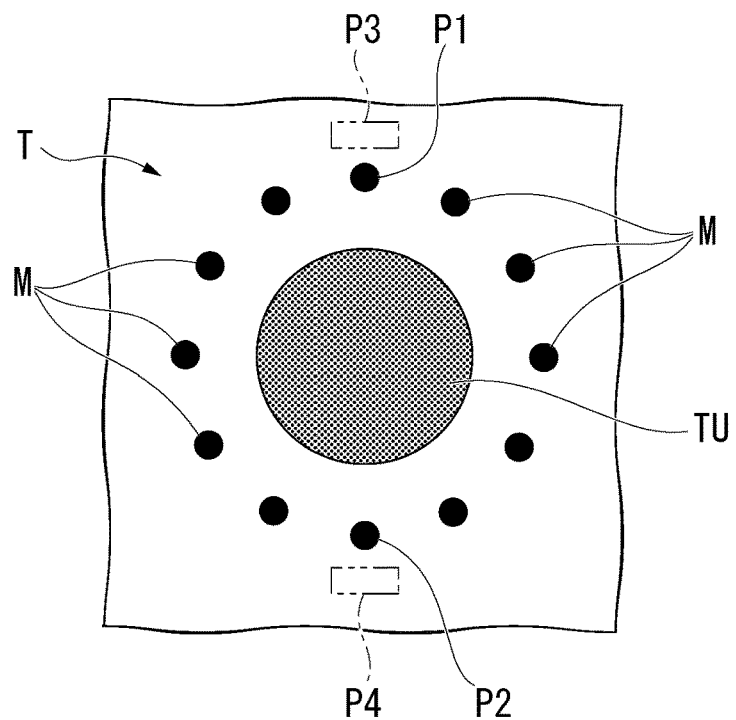
FIG. 13 is a view showing the marking step in the present suture method.

As shown in FIG. 13, the surgeon applies a marking M by pressing the knife N1 of the high-frequency knife N to cauterize the peripheral tissues surrounding the tumor (lesion) TU as the treatment target T. In the present embodiment, the marking M is applied by cauterizing the mucosal layer M1, and the marking M does not reach the submucosa layer M2 and the muscular layer M3.

In a case in which the following arrangement step or the like can be carried out without the marking M, the surgeon may omit the marking step. When the marking is finished, the surgeon removes the high-frequency knife N from the treatment device channel 230.

Selecting Step

The surgeon selects a first position P1 and a second position P2 to be grasped by using the grasping forceps G. The first position P1 and the second position P2 are the portion of the marking M or the portion outside the marking M. Here, the recitation "outside" means the direction apart from the tumor TU. In the present embodiment, the first position P1 and the second position P2 are at two sides of the tumor TU to sandwich the tumor TU therebetween. The first position P1 and the second position P2 are not necessary to be at the two sides of the tumor TU to sandwich the tumor TU therebetween.

Arrangement Step

The surgeon inserts the grasping forceps G as the treatment device for retraction (first treatment device) and protrudes a first grasping piece g1 and a second grasping piece g2 that are disposed at the distal end of the grasping forceps G from the forceps port 214.

Figure 14:
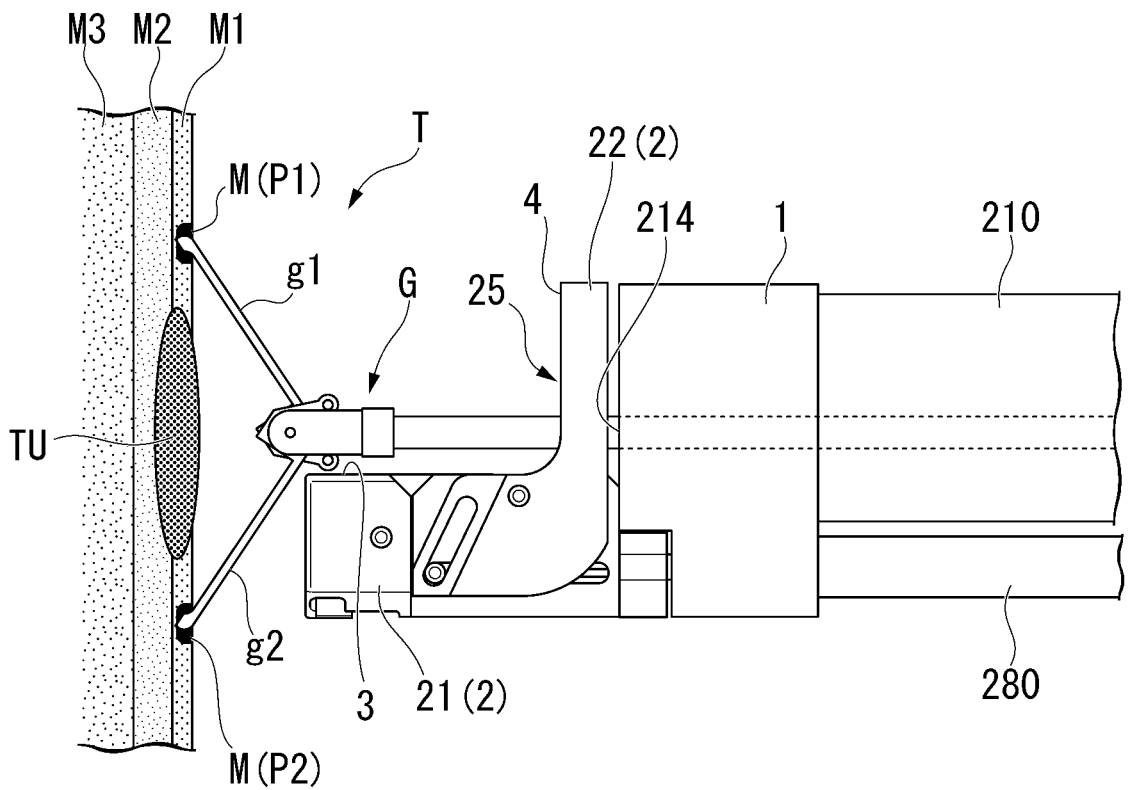
FIG. 14 is a view showing an arrangement step in the present suture method.

As shown in FIG. 14, the surgeon arranges the first grasping piece g1 at the first position P1 and hooks the first grasping piece g1 on the first position P1 (first arrangement step). Next, the surgeon pulls the first grasping piece g1 in the lower direction B1 while arranging the second grasping piece g2 at the second position P2 and hooking the second grasping piece g2 on the second position P2 (second arrangement step). As a result, the grasping forceps G enters the state shown in FIG. 14. The surgeon may perform the first arrangement step and the second arrangement step simultaneously.

Grasping Step

The surgeon presses the first grasping piece g1 and the second grasping piece g2 on the peripheral tissues of the tumor TU and closes the first grasping piece g1 and the second grasping piece g2 to grasp the peripheral tissues of the tumor TU.

Retraction Step

Figure 15:
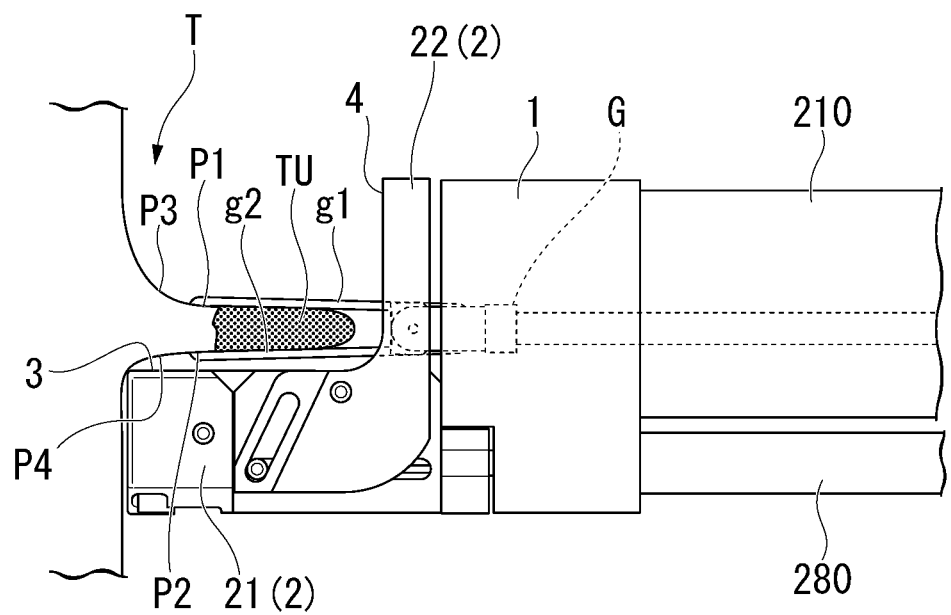
FIG. 15 is a view showing a retraction step in the present suture method.

The surgeon draws the first grasping piece g1 and the second grasping piece g2 together. As shown in FIG. 15, the surgeon pulls back the grasping forceps G toward the proximal end side in the state in which the peripheral tissues of the tumor TU are grasped by the first grasping piece g1 and the second grasping piece g2. The surgeon retracts the grasping forceps G so as to dispose the distal end of the grasping forceps G at the proximal end side of the staple extraction portion 3.

Figure 16:
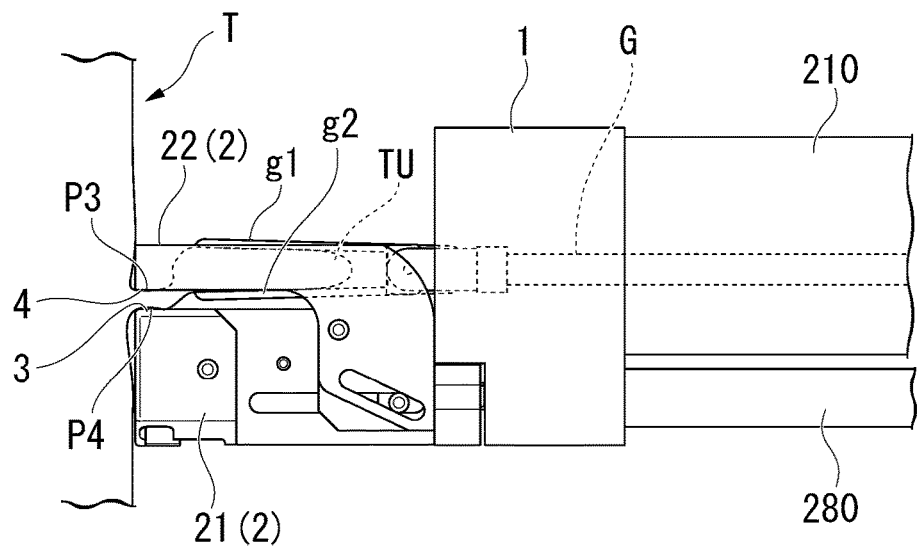
FIG. 16 is a view showing the retraction step in the present suture method.

As shown in FIG. 16, the surgeon operates the open-close operation portion 250 to retract the open-close operation wire 5 so as to make the grasping portion 2 to enter the closed state. The surgeon clamps a first suture position P3 (see FIG. 13) positioned at the more external side than the first position P1 with respect to the tumor TU and a second suture position P4 (see FIG. 13) positioned at the more external side than the second position P2 with respect to the tumor TU by the staple extraction portion 3 of the first grasping member 21 and the staple accommodation portion 4 of the second grasping member 22.

The surgeon clamps the first suture position P3 and the second suture position P4 at the more external side than the first position P1 and the second position P2 by the staple extraction portion 3 and the staple accommodation portion 4 in the state in which the first grasping piece g1 and the second grasping piece g2 grasping the first position P1 and the second position P2 are disposed at the more proximal end side than the stable extraction portion 3. Accordingly, the tumor TU positioned at the internal side of the first position P1 and the second position P2 are disposed at the more proximal end side than the staple extraction portion 3.

When the grasping portion 2 is in the closed state, at least part of the tumor TU disposed at the proximal end side than the staple extraction portion 3 is accommodated in the space (view space 25) formed by the U-shaped member 22a and the second main body portion 22b of the second grasping member 22 such that the grasping operation is not obstructed by the first grasping member 21 and the second grasping member 22.

When the grasping portion 2 is in the closed state, as shown in FIG. 8, the optical axis A1 of the object lens 215 pass through the upper side B1 of the first grasping member 21 and the second grasping member 22. Accordingly, the surgeon may observe the treatment target T by the imaging unit of the endoscope 200 even the grasping portion 2 is in the closed state.

Suture Step

The surgeon operates the extraction operation portion 270 to pull the extraction-operation wire 6 in the state in which the first suture position P3 and the second suture position P4 are clamped by the staple extraction portion 3 and the staple accommodation portion 4 so as to eject the accommodated staple S toward the staple accommodation portion 4. The needle tip S1 of the staple S penetrates the first suture position P3 and the second suture position P4 to come into contact with the pocket 41 of the staple accommodation portion 4 so as to be bent. As a result, the first suture position P3 and the second suture position P4 are sutured together.

Figure 17:
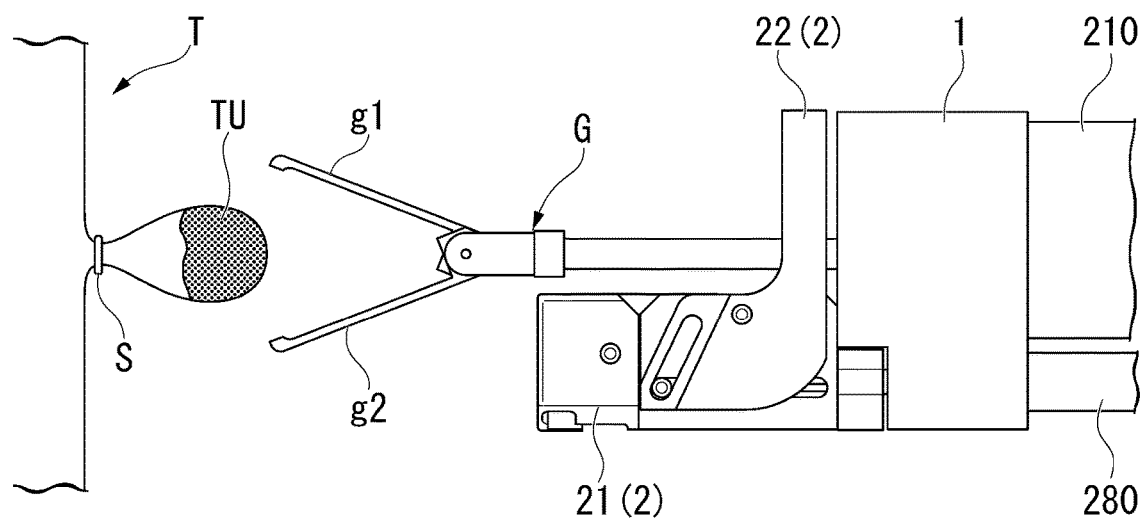
FIG. 17 is a view showing a suturing step in the present suture method.

As shown in FIG. 17, the surgeon operates the open-close operation portion 250 to make the grasping portion 2 into the open state again. The surgeon opens the grasping forceps G and puts the grasping forceps G away from the treatment target T.

Here, it is described that the surgeon puts the grasping forceps G away from the treatment target T after suturing the tissues; however, the surgeon may put the grasping forceps G away from the treatment target T at any time after making the grasping portion 2 into the closed state in the retraction step.

Resection Step

Figure 18:
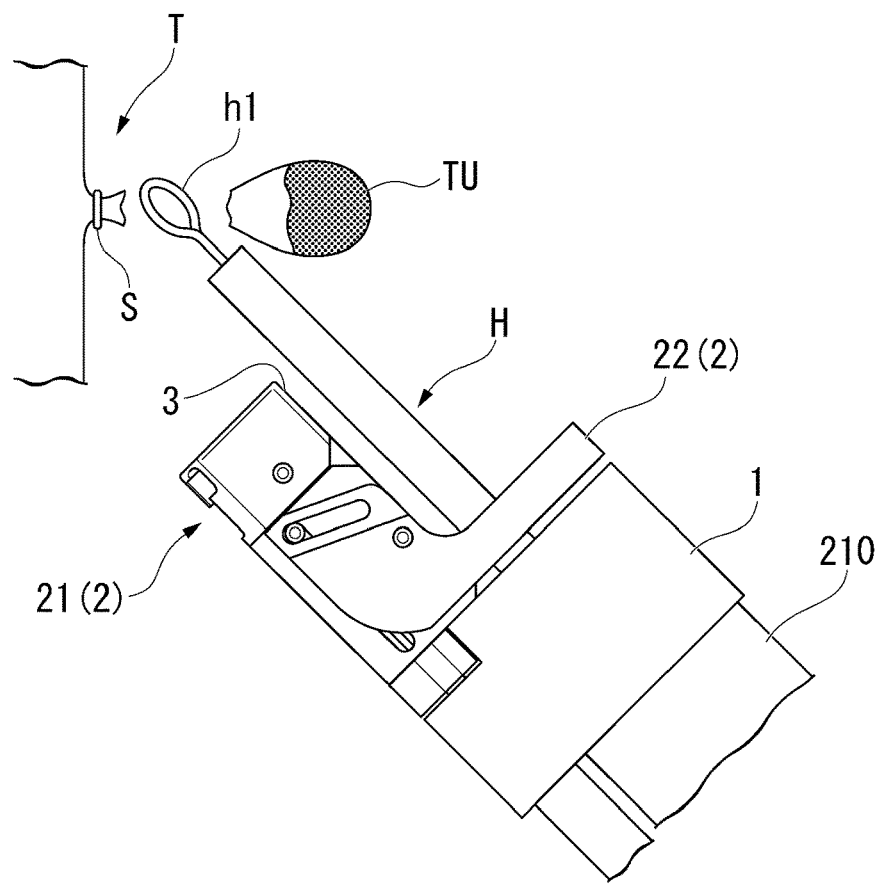
FIG. 18 is a view showing a resection step in the present suture method.

The surgeon removes the grasping forceps G from the treatment device channel 230, then inserts a high-frequency snare H as a treatment device for resection (second treatment device) and protrudes the snare wire h1 disposed at the distal end of the high-frequency snare H from the forceps port 214. As shown in FIG. 18, the surgeon resects the lesion site including the tumor TU at the more proximal end side (the tumor TU side) than the portion being sutured by the staple S. More specifically, the surgeon resects the portion including the tumor TU and without the sutured portion. The tumor TU is disposed at the proximal end side of the sutured portion (the first suture position P3 and the second suture position P4) such that the surgeon may definitely resect the whole tumor TU. The surgeon may definitely resect the whole tumor TU even if the tumor TU reaches the submucosa layer M2. The surgeon recycles the resected tumor TU and finishes the suture procedures.

According to the suture method described in the present embodiment, it is possible to retract the whole tumor TU into the medical stapler 100 and suture the first suture position P3 at the external side of the first position P1 and the second suture position P4 at the external side of the second position P2 in the peripheral tissues of the tumor TU. Accordingly, the surgeon may definitely resect the whole tumor TU.

Although the first embodiment of the present disclosure has been described above, the specific configuration of the present disclosure is not limited to the above-described embodiment, and configurations in the respective embodiments and modifications within the scope not departing from the spirit of the present disclosure.

Modification 1-1

Figure 19:
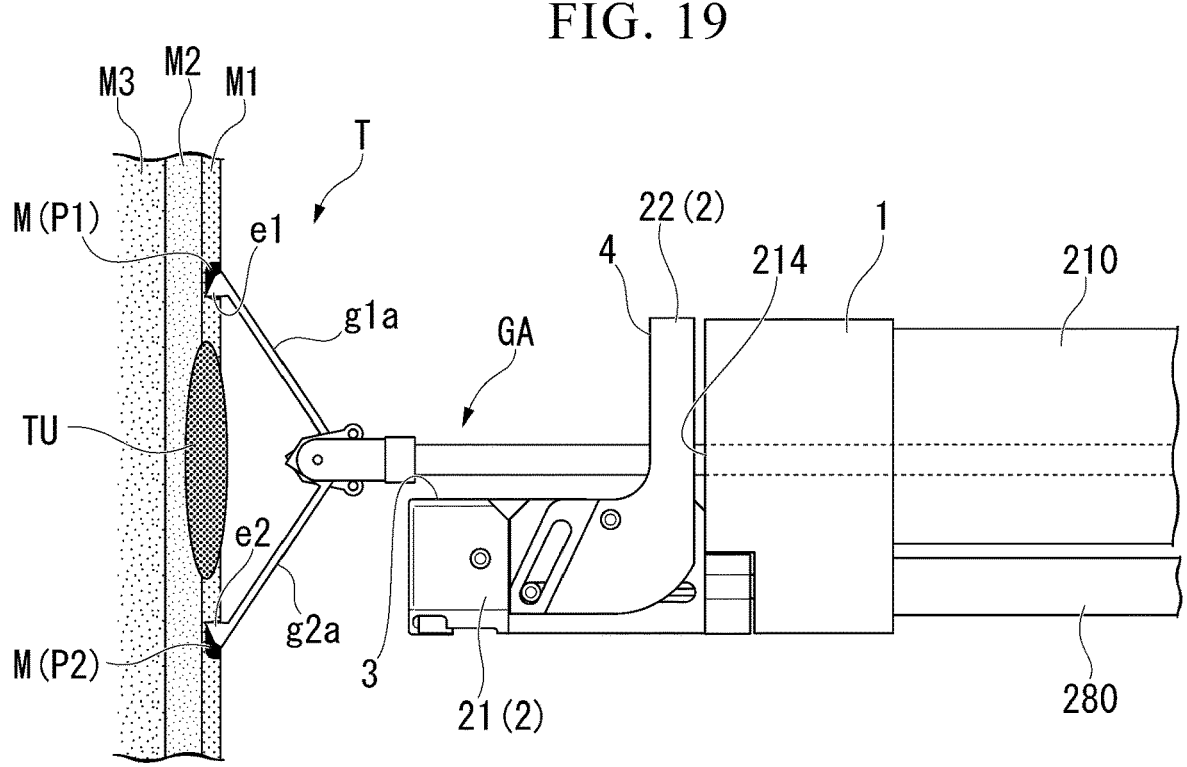
FIG. 19 is a view showing a modification of the arrangement step in the present suture method.

In the above-described embodiment, the grasping forceps G as the treatment device for retraction (first treatment device) is used in the arrangement step and the grasping step; however, the aspects of the arrangement step and the grasping step are not limited thereto. FIG. 19 is a view showing the arrangement step using a grasping forceps GA as the treatment device for retraction (first treatment device). The grasping forceps GA includes a first grasping piece g1a and a second grasping piece g2a. A first engaging claw e1 being convex toward the second grasping piece g2a side is provided in the distal end of the first grasping piece g1a. The first engaging claw e1 protrudes in a direction orthogonal to the longitudinal direction of the first grasping piece g1a. A second engaging claw e2 being convex toward the first grasping piece g1a side is provided in the distal end of the second grasping piece g2a. The second engaging claw e2 protrudes in a direction orthogonal to the longitudinal direction of the second grasping piece g2a.

According to the grasping step using the grasping forceps GA, even in a state in which the depth of the marking M is shallow, it is possible to firmly grasp the first position P1 and the second position P2 by the first engaging claw e1 and the second engaging claw e2. According to the grasping step using the grasping forceps GA, it is possible to firmly grasp the tissues so as to suitably grasp the tissues in the portion without any marking M.

Modification 1-2

Figure 20:
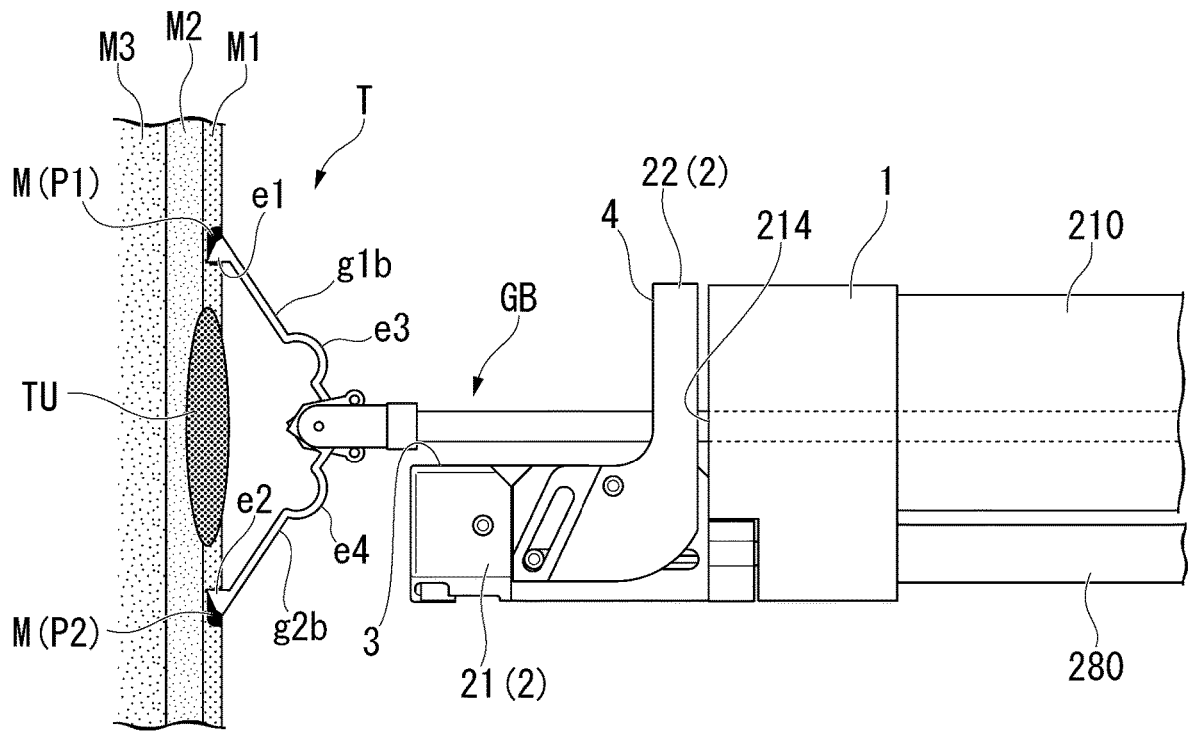
FIG. 20 is a view showing another modification of the arrangement step in the present suture method.

In the above-described embodiment, the grasping forceps G as the treatment device for retraction (first treatment device) is used in the arrangement step and the grasping step; however, the aspects of the arrangement step and the grasping step are not limited thereto. FIG. 20 is a view showing the arrangement step using a grasping forceps GB as the treatment device for retraction (first treatment device). The grasping forceps GB includes a first grasping piece g1b and a second grasping piece g2b. A first engaging claw e1 being convex toward the second grasping piece g2b side is provided in the distal end of the first grasping piece g1b. A first expanding portion e3 expanding outwardly (the opening direction of the open-closed direction) is formed in the proximal end side of the first grasping piece g1b. A second engaging claw e2 being convex toward the first grasping piece g1b side is provided in the distal end of the second grasping piece g2b. A second expanding portion e4 expanding outwardly (the opening direction of the open-closed direction) is formed in the proximal end side of the second grasping piece g2b.

Figure 21:
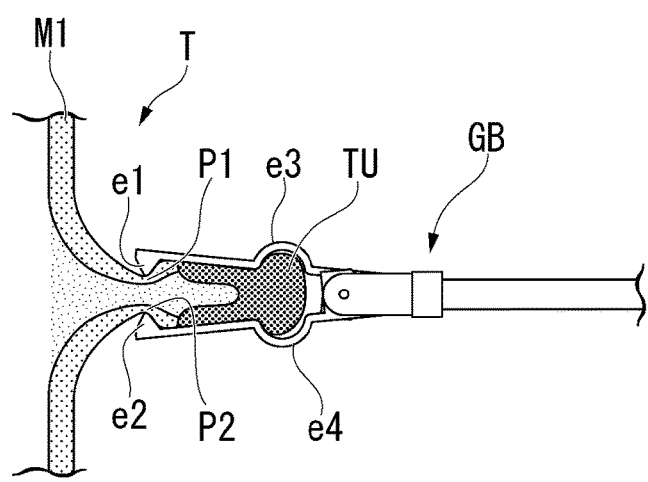
FIG. 21 is a view showing a modification of a grasping step in the present suture method.

FIG. 21 is a view showing the grasping step using the grasping forceps GB as the treatment device for retraction (first treatment device). The grasping forceps GB includes the first expanding portion e3 and the second expanding portion e4 and it is possible to firmly grasp the tissues by clamping the tissues including the tumor TU between the first grasping piece g1b and the second grasping piece g2b even if the tumor TU is large.

Second Embodiment

A second embodiment of the present disclosure will be described with reference to FIG. 22 to FIG. 24. Hereinafter, the same configurations that have been described above will be designated to the same references, the description thereof will be omitted, and differences from the above embodiment will be mainly described. A suture method according to the second embodiment is performed by using the medical system 300 according to the first embodiment, for example.

Usage of Medical Stapler 100

Hereinafter, the usage of the medical stapler 100 (suture method using the medical stapler 100) will be described. FIG. 22 to FIG. 24 are figures for descripting the usage of the medical stapler 100.

Insertion Step

The surgeon inserts the insertion portion 210 of the endoscope 200 to which the medical stapler 100 is attached from the mouth as the natural orifice and approaches the distal end portion 211 to the treatment target T. The surgeon operates the open-close operation portion 250 to advance the open-close operation wire 5 and make the grasping portion 2 into the open state.

Marking Step

Figure 22:
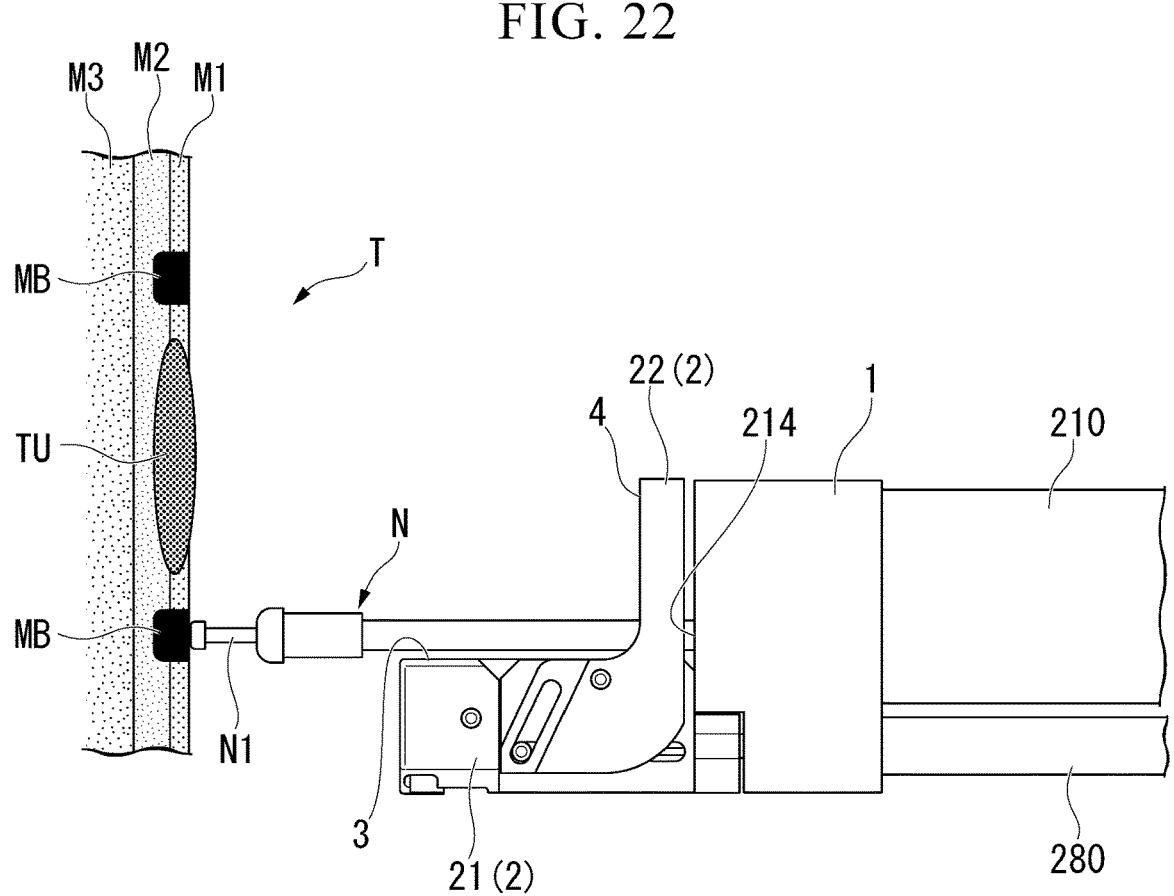
FIG. 22 is a view showing a marking step in a suture method according to a second embodiment of the present disclosure.

As shown in FIG. 22 and similar to the first embodiment, the surgeon inserts the high-frequency knife N as the treatment device for marking (third treatment device) into the treatment device channel 230, and protrudes the knife N1 disposed at the distal end of the high-frequency knife N from the forceps port 214.

Figure 23:
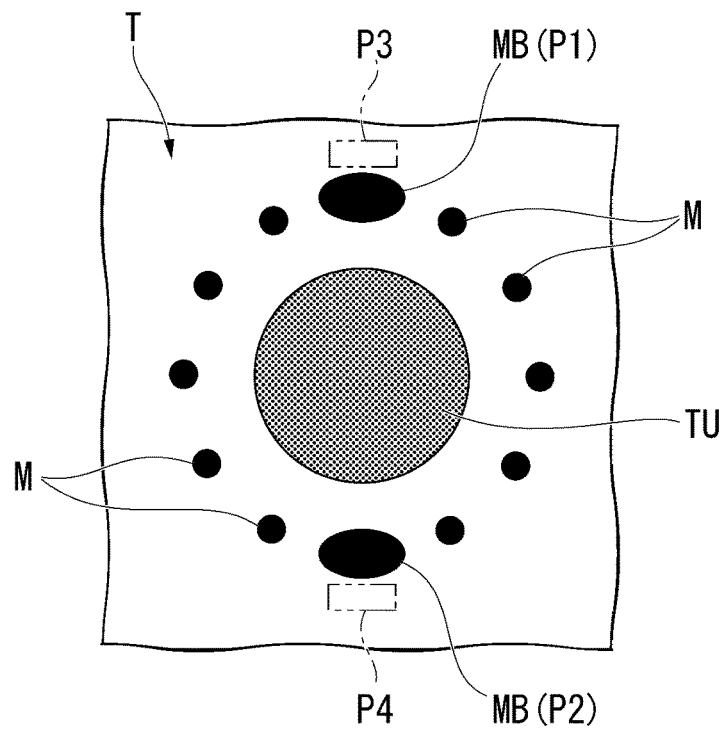
FIG. 23 is a view showing the marking step in the present suture method.

As shown in FIG. 23, the surgeon applies a marking M and a marking MB by pressing the knife N1 of the high-frequency knife N to cauterize the peripheral tissues surrounding the tumor (lesion) TU as the treatment target T. In the present embodiment, the marking MB is applied by cauterizing the mucosal layer M1 and the submucosa layer M2, and the marking MB does not reach the muscular layer M3. The depth of the marking MB is relatively deeper than that of the marking M.

Figure 24:
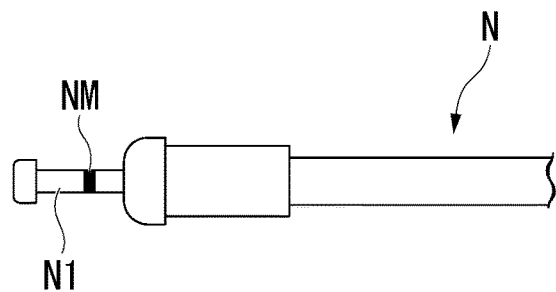
FIG. 24 is a view showing a high-frequency knife as an example used in the marking step in the present suture method.

FIG. 24 is a view showing the high-frequency knife N having the marking NM.

The knife N1 of the high-frequency knife N may have the marking NM which is capable of visually confirming the insertion amount of the knife N1 inserting into the tissues when forming the marking MB. The surgeon may easily and accurately form the marking MB reaching the submucosa layer M2 by cauterizing the tissues while confirming the marking NM. When the marking is finished, the surgeon removes the high-frequency knife N from the treatment device channel 230.

Selecting Step

The surgeon selects the portion of the marking MB as the first position P1 and the second position P2. As shown in FIG. 23, the surgeon may form the marking MB only in the portion that is selected as the first position P1 and the second position P2.

Arrangement Step

The surgeon inserts the grasping forceps G as the treatment device for retraction (first treatment device) and protrudes a first grasping piece g1 and a second grasping piece g2 that are disposed at the distal end of the grasping forceps G from the forceps port 214.

The surgeon arranges the first grasping piece g1 at the first position P1 and hooks the first grasping piece g1 on the first position P1 (first arrangement step). Next, the surgeon pulls the first grasping piece g1 in the lower direction B1 while arranging the second grasping piece g2 at the second position P2 and hooking the second grasping piece g2 on the second position P2 (second arrangement step). As a result, the grasping forceps G enters the state shown in FIG. 26. The surgeon may perform the first arrangement step and the second arrangement step simultaneously.

Grasping Step

The surgeon presses the first grasping piece g1 and the second grasping piece g2 on the peripheral tissues of the tumor TU and closes the first grasping piece g1 and the second grasping piece g2 to grasp the peripheral tissues of the tumor TU. The first position P1 and the second position P2 are the portions being marked as the marking MB, and the depth is relatively deeper than that according to the first embodiment. Accordingly, the surgeon may firmly grasp the tissues.

Retraction Step to Resection Step

Similar to the first embodiment, the surgeon performs the retraction step and the resection step to finish the suture procedures.

According to the suture method described in the present embodiment, it is possible to retract the whole tumor TU into the medical stapler 100 and suture the first suture position P3 positioned at the more external side than the first position P1 and the second suture position P4 positioned at the more external side than the second position P2 in the peripheral tissues of the tumor TU. Accordingly, it is possible for the surgeon to definitely resect the whole tumor TU.

Although the second embodiment of the present disclosure has been described above with reference to the figures, the specific configuration of the present disclosure is not limited to the above-described embodiment, and configurations in the respective embodiments and modifications within the scope not departing from the spirit of the present disclosure.

Modification 2-1

Figure 25:
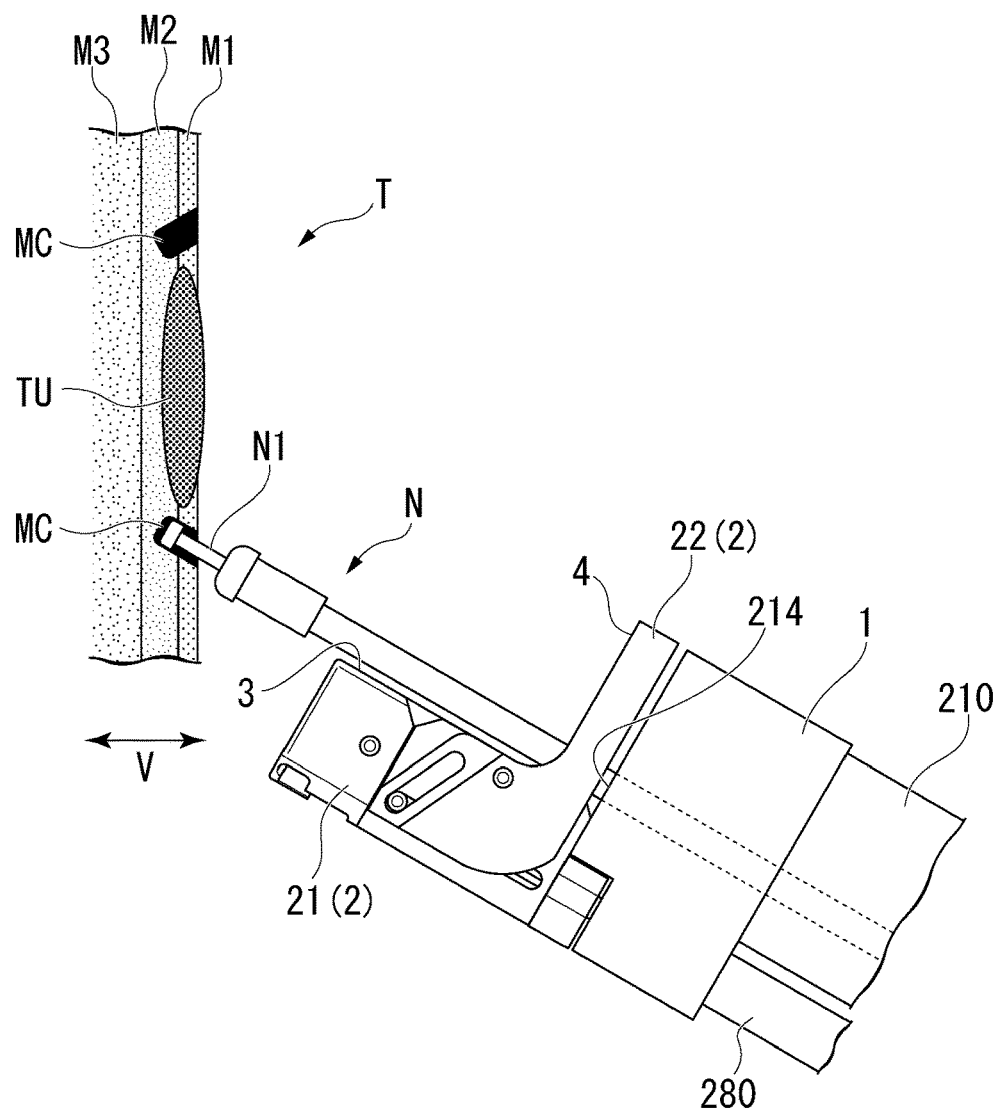
FIG. 25 is a view showing a modification of the marking step in the present suture method.

In the above-described embodiment, the marking MB formed in the marking step is formed along a vertical direction V orthogonal to the surface of the peripheral tissues of the tumor TU. However, the aspect of the marking step is not limited thereto. FIG. 25 is a view showing a modification of the marking step. The surgeon may form a marking MC along a direction inclined to the surface of the peripheral tissues of the tumor TU. The marking MC is formed along the direction inclined with respect to the vertical direction V, and the marking MC is formed such that the marking MC approaches the tumor TU with the depth of the marking MC increases.

Figure 26:
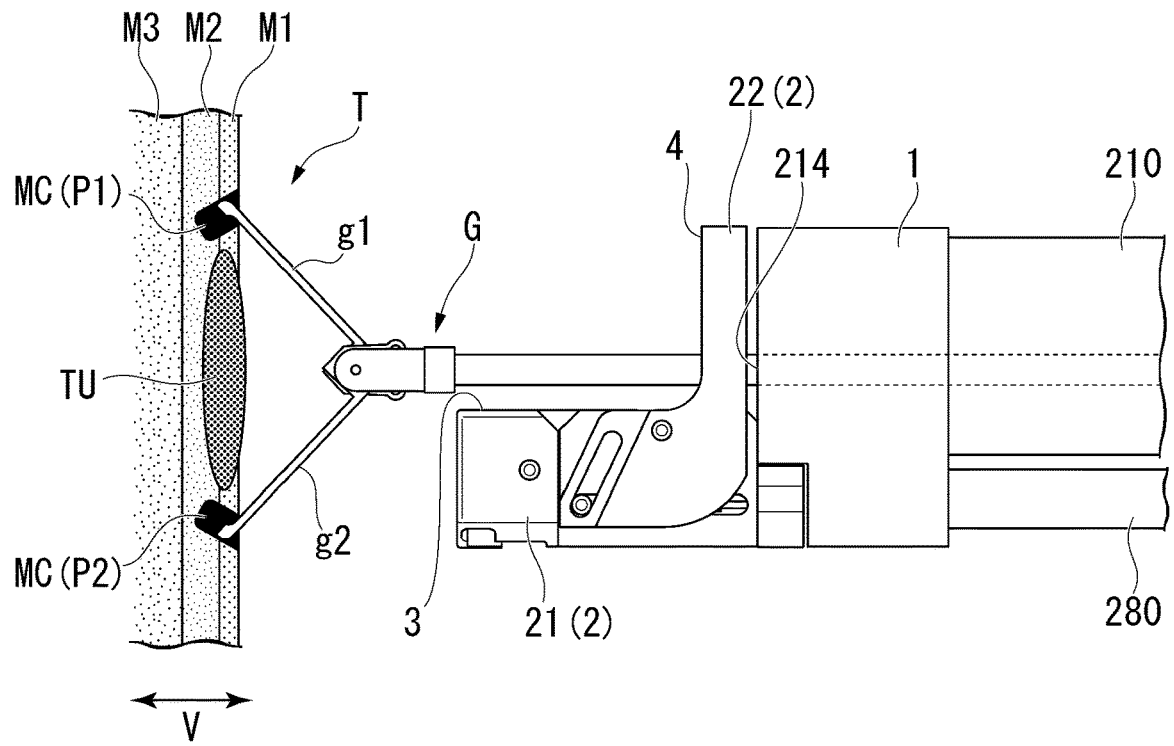
FIG. 26 is a view showing a modification of the arrangement step in the present suture method.

FIG. 26 is a view showing the arrangement step in a case in which the marking MC is formed as the first position P1 and the second position P2. Since the marking MC is formed such that the marking MC approaches the tumor TU with the depth of the marking MC increases, the surgeon may firmly grasp more tissues once. The surgeon may grasp the marking MC by using the grasping forceps GA disclosed in the modification 1-1 or the grasping forceps GB disclosed in the modification 1-2. The surgeon may definitely grasp the tissues.

Modification 2-2

Figure 27:
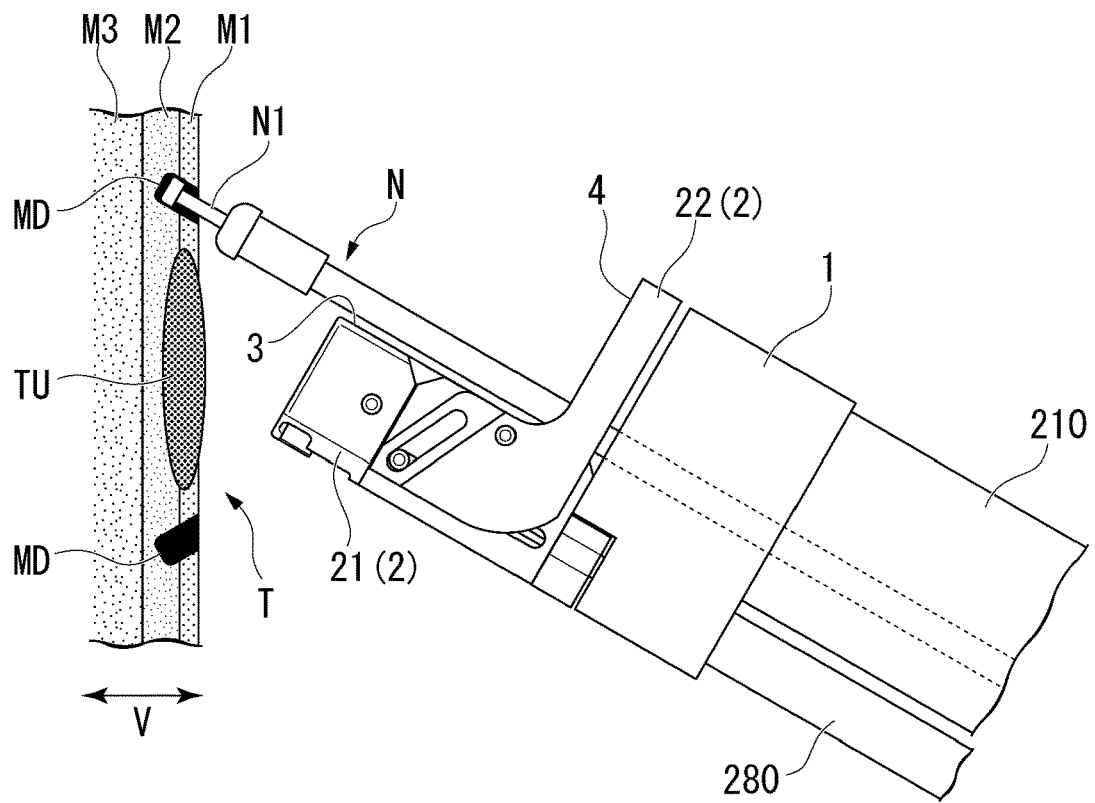
FIG. 27 is a view showing another modification of the marking step in the present suture method.

In the above-described embodiment, the marking MB formed in the marking step is formed along a vertical direction V orthogonal to the surface of the peripheral tissues of the tumor TU. However, the aspect of the marking step is not limited thereto. FIG. 27 is a view showing a modification of the marking step. The surgeon may form a marking MD along a direction inclined to the surface of the peripheral tissues of the tumor TU. The marking MD is formed along the direction inclined to the vertical direction V, and the marking MD is formed such that the marking MD is apart away from the tumor TU with the depth of the marking MD increases.

Figure 28:
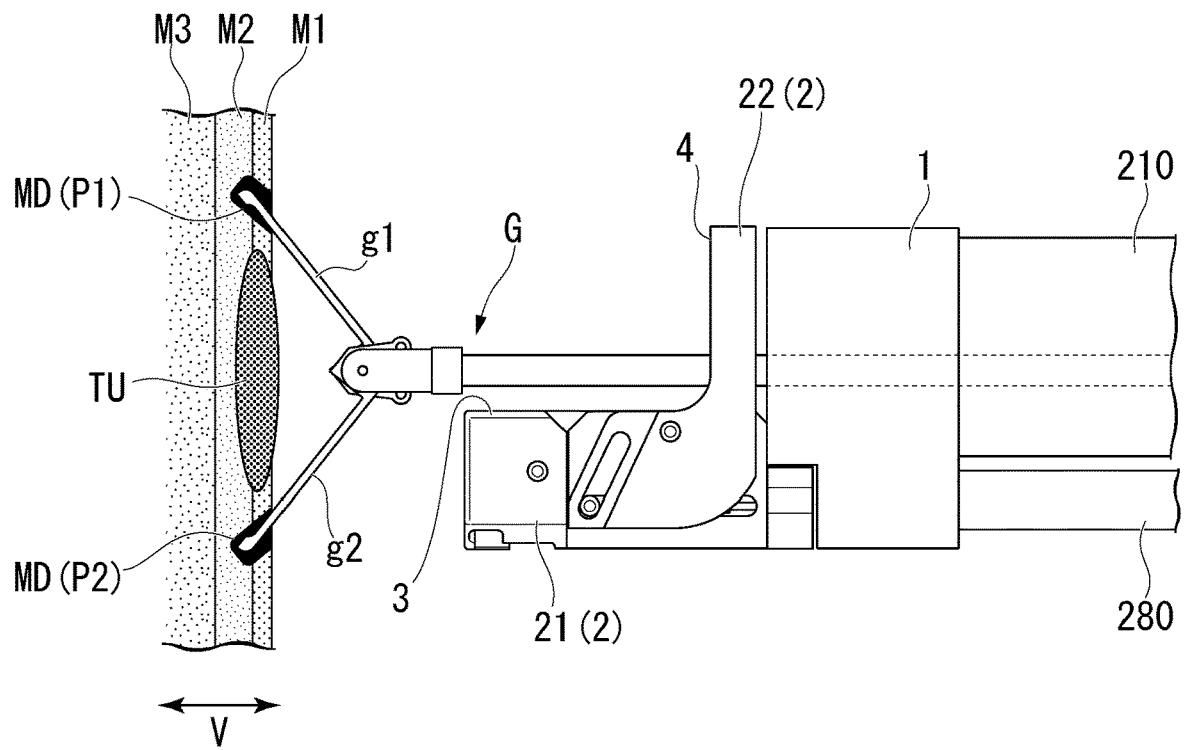
FIG. 28 is a view showing another modification of the arrangement step in the present suture method.

FIG. 28 is a view showing the arrangement step in a case in which the marking MD is formed as the first position P1 and the second position P2. Since the marking MD is formed such that the marking MD is apart away from the tumor TU with the depth of the marking MD increases, it is easy for the surgeon to insert and arrange the first grasping piece g1 and the second grasping piece g2 into the marking MD.

Figure 29:
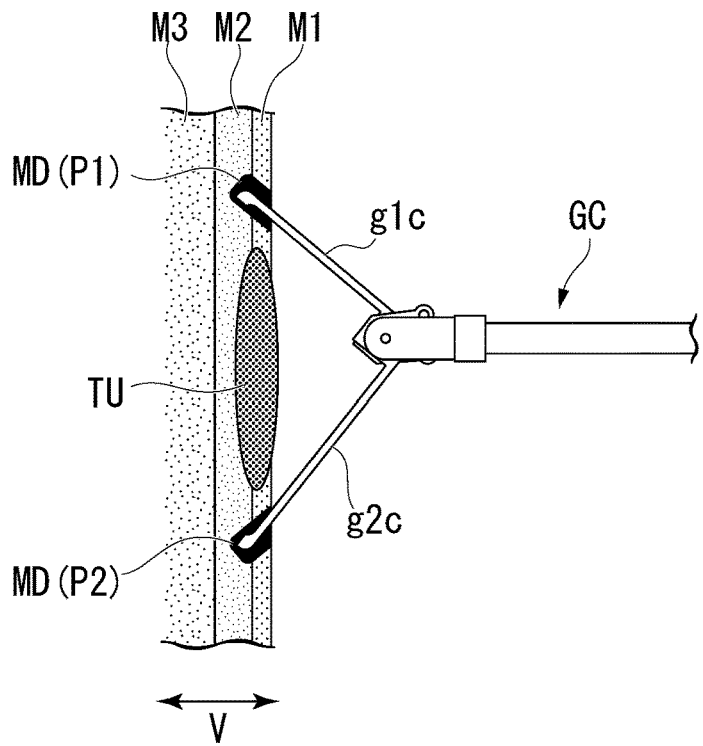
FIG. 29 is a view showing another modification of the arrangement step in the present suture method.

FIG. 29 is a view showing a modification of the arrangement step using a grasping forceps GC. The grasping forceps GC includes a first grasping piece g1c and a second grasping piece g2c. The second grasping piece g2c is longer than the first grasping piece g1c. The surgeon hooks the second grasping piece g2c to the second position P2 (second arrangement step). After the second grasping step, the surgeon hooks the first grasping piece g1c to the first position P1 (first arrangement step). The surgeon may insert the first grasping piece g1c and the second grasping piece g2c of the grasping forceps GC into the marking MD more easily.

Third Embodiment

A third embodiment of the present disclosure will be described with reference to FIG. 30 to FIG. 32. Hereinafter, the same configurations that have been described above will be designated to the same references, the description thereof will be omitted, and differences from the above embodiment will be mainly described. A suture method according to the second embodiment is performed by using the medical system 300 according to the first embodiment, for example. However, the endoscope used in the suture method according to the third embodiment includes two treatment device channels 230. In the following description, the two treatment device channels 230 are referred to as a first treatment tool channel and a second treatment tool channel.

Usage of Medical Stapler 100

Hereinafter, the usage of the medical stapler 100 (suture method using the medical stapler 100) will be described. FIG. 30 to FIG. 34 are figures for descripting the usage of the medical stapler 100.

Insertion Step

The surgeon inserts the insertion portion 210 of the endoscope 200 to which the medical stapler 100 is attached from the mouth as the natural orifice and approaches the distal end portion 211 to the treatment target T. The surgeon operates the open-close operation portion 250 to advance the open-close operation wire 5 and make the grasping portion 2 into the open state.

Marking Step

Similar to the first embodiment, the surgeon inserts the high-frequency knife N as the treatment device for marking (third treatment device) into the treatment device channel 230, and protrudes the knife N1 disposed at the distal end of the high-frequency knife N from the forceps port 214.

Figure 30:
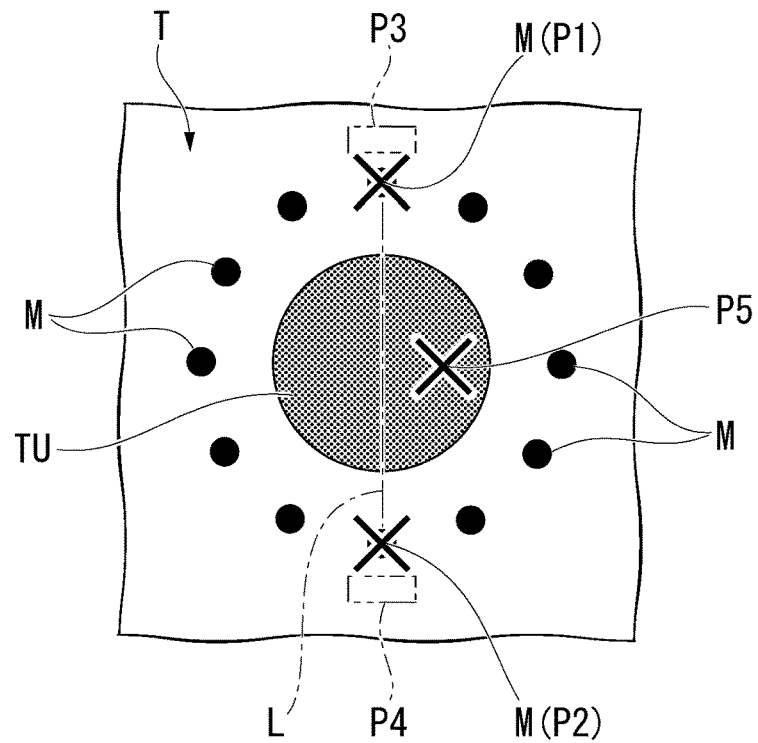
FIG. 30 is a view showing a marking step in a suture method according to a third embodiment of the present disclosure.
Figure 31:
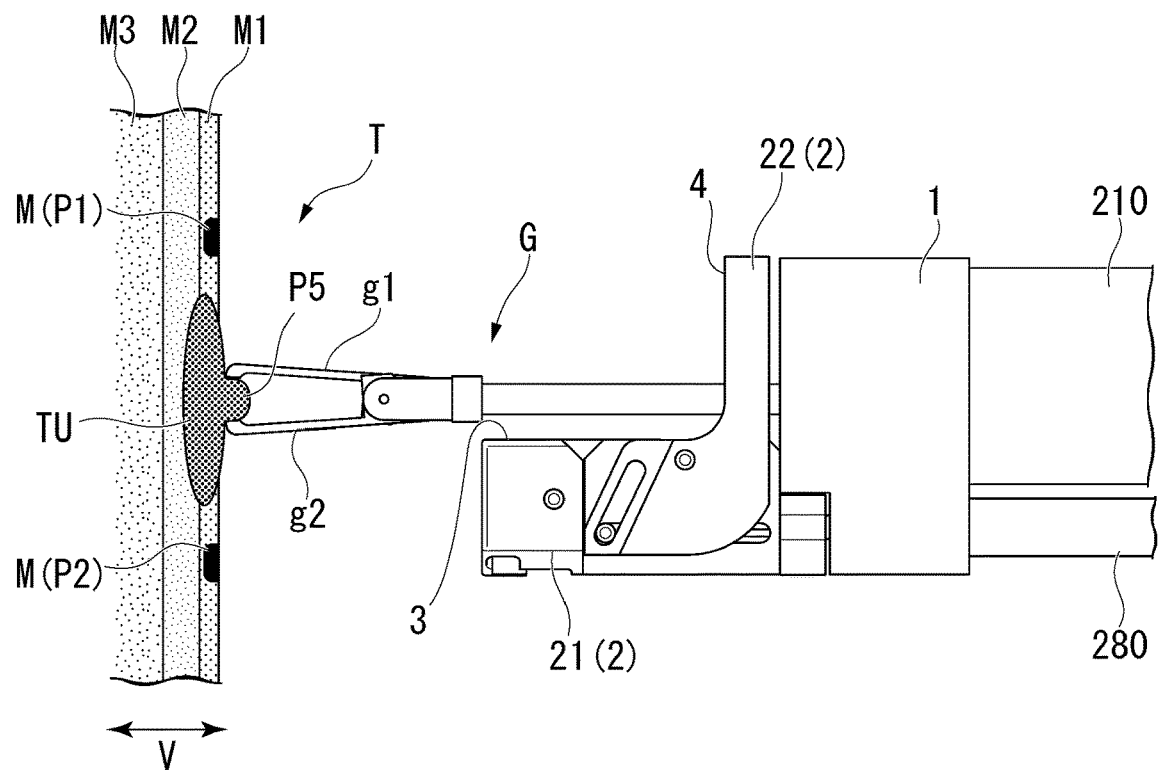
FIG. 31 is a view showing an assistance grasping step in the present suture method.

As shown in FIG. 30, the surgeon applies the marking M by pressing the knife N1 of the high-frequency knife N to cauterize the peripheral tissues surrounding the tumor (lesion) TU as the treatment target T. When the marking is finished, the surgeon removes the high-frequency knife N from the treatment device channel 230.

Selecting Step

The surgeon selects the portion of the marking M or the portion outside the marking M as the first position P1 and the second position P2. Furthermore, the surgeon selects a position in the vicinity of the center of the tumor TU as an assistance position P5. As shown in FIG. 30, it is desired that the assistance position P5 is slightly apart away from a line L connecting the first position P1 and the second position P2.

Arrangement Step and Grasping Step

The surgeon inserts the grasping forceps G as the treatment device for retraction assistance (fourth treatment device) and protrudes the first grasping piece g1 and the second grasping piece g2 disposed at the distal end of the grasping forceps G from the forceps port 214. As shown in FIG. 31, the surgeon grasps the assistance position P5 of the tumor TU by the first grasping piece g1 and the second grasping piece g2 (assistance grasping step).

The surgeon inserts the grasping forceps GD as the treatment device for retraction (first treatment device) into the second treatment device channel. The grasping forceps GD includes a fixed forceps piece g10, a first forceps piece g11, and a second forceps piece g12. The first forceps piece g11 and the second forceps piece g12 are provided at two sides of the fixed forceps piece g10 to sandwich the fixed forceps piece g10 and to be individually rotatable.

Figure 32:
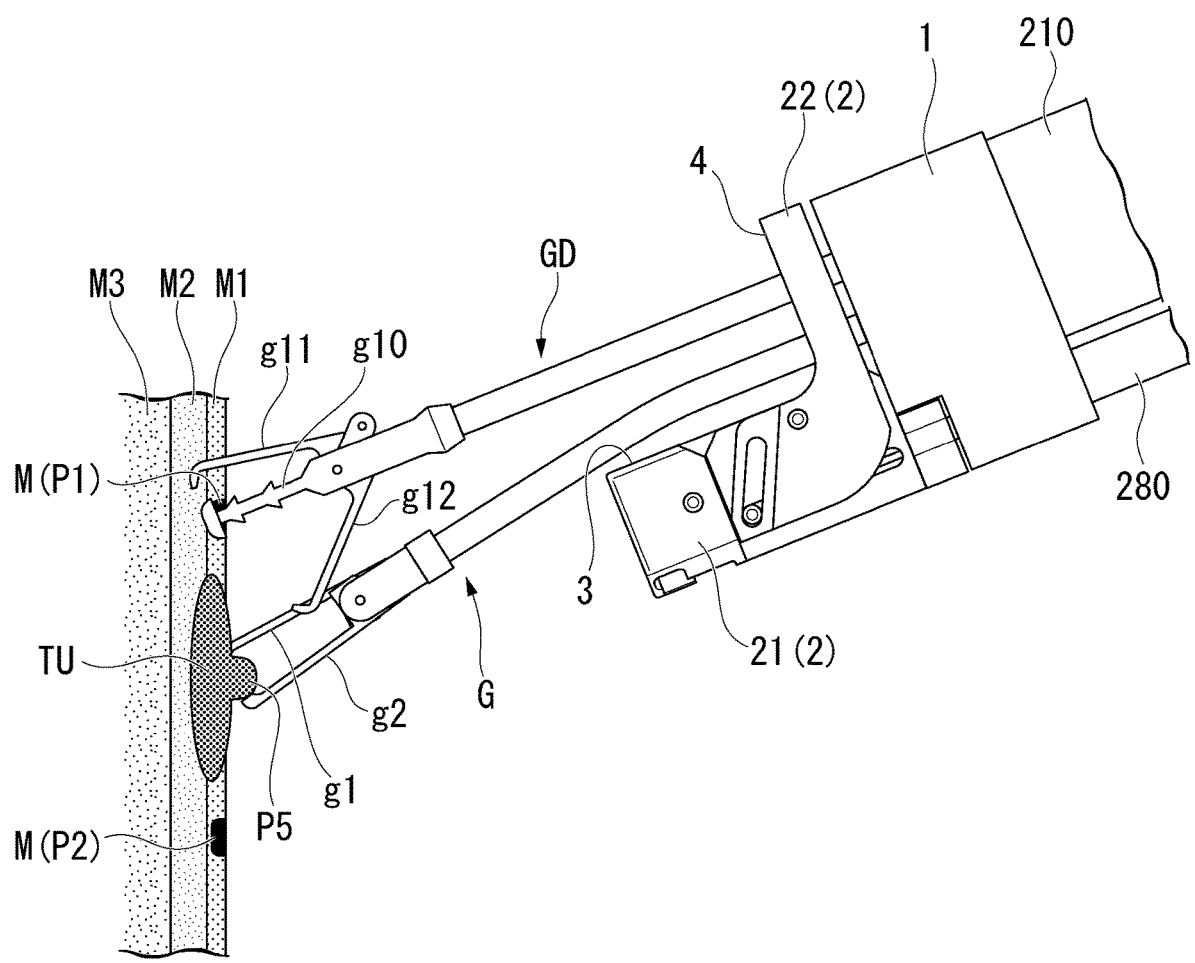
FIG. 32 is a view showing a first arrangement step and a first grasping step in the present suture method.

As shown in FIG. 32, the surgeon arranges the fixed forceps piece g10 to the first position P1. Next, the surgeon closes the first forceps piece g11 disposed on the external side of the fixed forceps piece g10 to clamp the first position P1 by the first forceps piece g11 and the fixed forceps piece g10 and hooks the fixed forceps piece g10 to the first position P1 (first arrangement step). Next, the surgeon presses the peripheral tissues of the tumor TU by the first forceps piece g11 and the fixed forceps piece g10 while closing the first forceps piece g11 and the fixed forceps piece g10 to grasp the peripheral tissues of the tumor TU (first grasping step).

Figure 33:
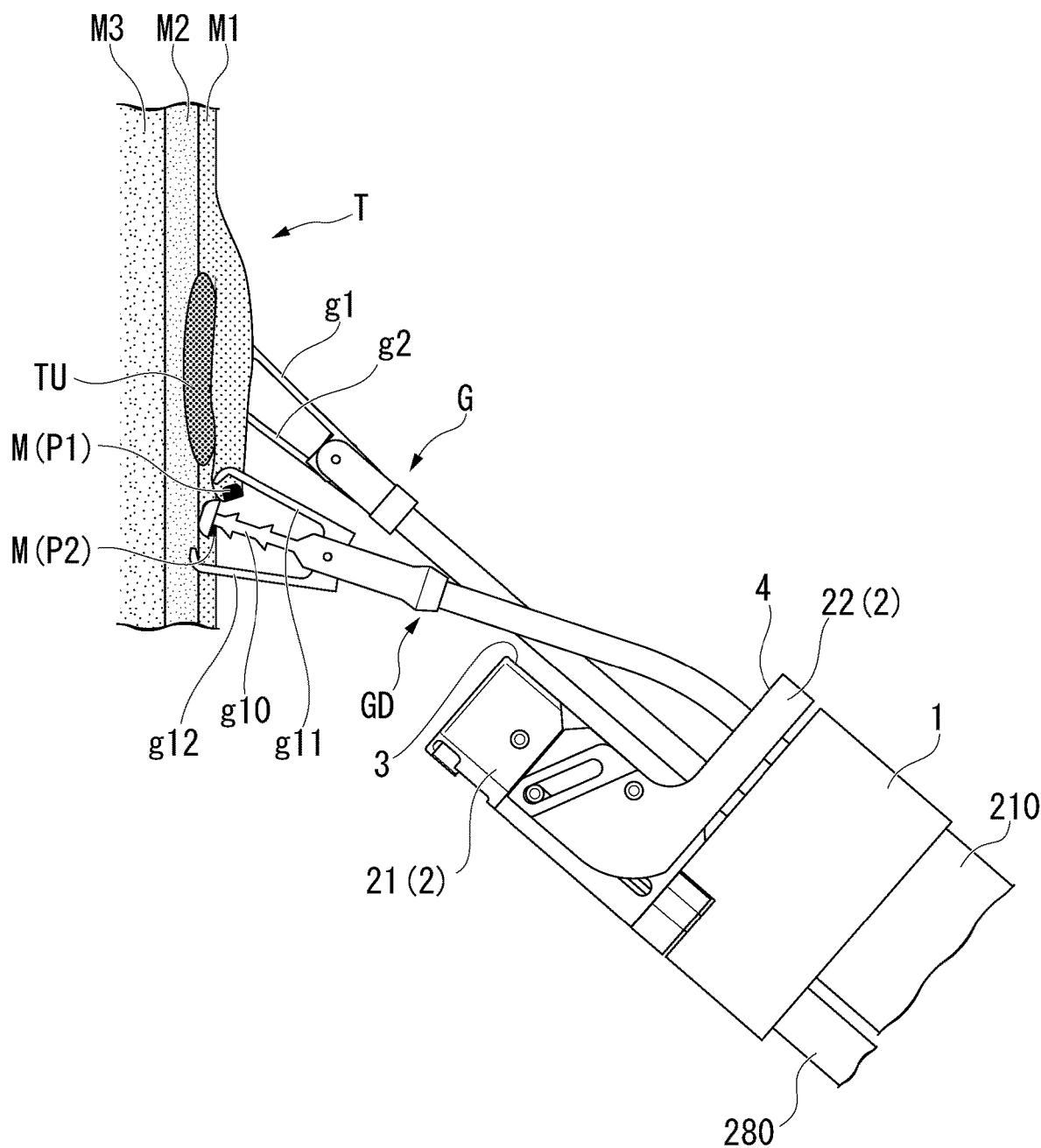
FIG. 33 is a view showing a second arrangement step and a second grasping step in the present suture method.

As shown in FIG. 33, the surgeon arranges the fixed forceps piece g10 to the second position P2. The first position P1 clamped by the first forceps piece g11 and the fixed forceps piece g10 is drawn to the vicinity of the second position P2. Next, the surgeon closes the second forceps piece g12 disposed on the external side of the fixed forceps piece g10 to clamp the second position P2 by the second forceps piece g12 and the fixed forceps piece g10 and hooks the fixed forceps piece g10 to the second position P2 (second arrangement step). Next, the surgeon presses the peripheral tissues of the tumor TU by the second forceps piece g12 and the fixed forceps piece g10 while closing the second forceps piece g12 and the fixed forceps piece g10 to grasp the peripheral tissues of the tumor TU (second grasping step).

As shown in FIG. 30, the assistance position P5 is slightly apart away from the line connecting the first position P1 and the second position P2 such that the surgeon may avoid the interference with the grasping forceps G grasping the assistance position P5 and move the grasping forceps GD from the first position P1 to the second position P2.

Retraction Step

The surgeon pulls back the grasping forceps GD toward the proximal end side in the state in which the peripheral tissues of the tumor TU are grasped by the first forceps piece g11 and the second forceps piece g12. The surgeon retracts the grasping forceps GD toward the proximal end side while retracing the grasping forceps G grasping the assistance position P5 toward the proximal end side. The surgeon retracts the grasping forceps GD and the grasping forceps G so as to make the distal end of the grasping forceps GD and the distal end of the grasping forceps G to be disposed at the more proximal end side of the staple extraction portion 3.

Suture Step to Resection Step

Similar to the first embodiment, the surgeon performs the suture step to the resection step so as to finish the suture procedures.

According to the suture method described in the present embodiment, the whole tumor may be definitely retracted by the medical stapler 100 using the grasping forceps GD and the grasping forceps G, and it is possible to suture the first suture position P3 positioned at the more external side than the first position P1 and the second suture position P4 positioned at the more external side than the second position P2 in the peripheral tissues of the tumor TU. Accordingly, the surgeon may definitely resect the whole tumor TU.

Although the third embodiment of the present disclosure has been described above with reference to the figures, the specific configuration of the present disclosure is not limited to the above-described embodiment, and configurations in the respective embodiments and modifications within the scope not departing from the spirit of the present disclosure.

Modification 3-1

Figure 34:
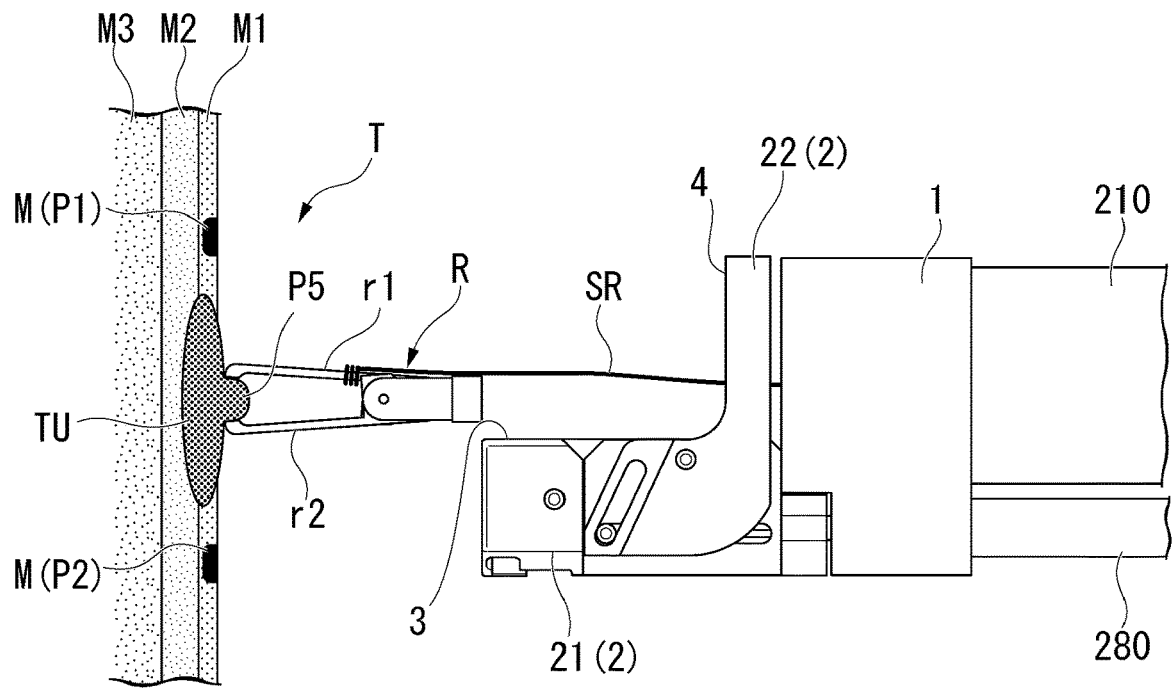
FIG. 34 is a view showing a modification of the assistance grasping step in the present suture method.

In the above-described embodiment, the grasping forceps G is used as the treatment device for retraction assistance (fourth treatment device). However, as shown in FIG. 34, the treatment device for retraction assistance (fourth treatment device) may be a clip with suture thread R. The surgeon grasps the assistance position P5 of the tumor TU by the first grasping piece r1 and the second grasping piece r2 of the clip with suture thread R (grasping assistance step).

Figure 35:
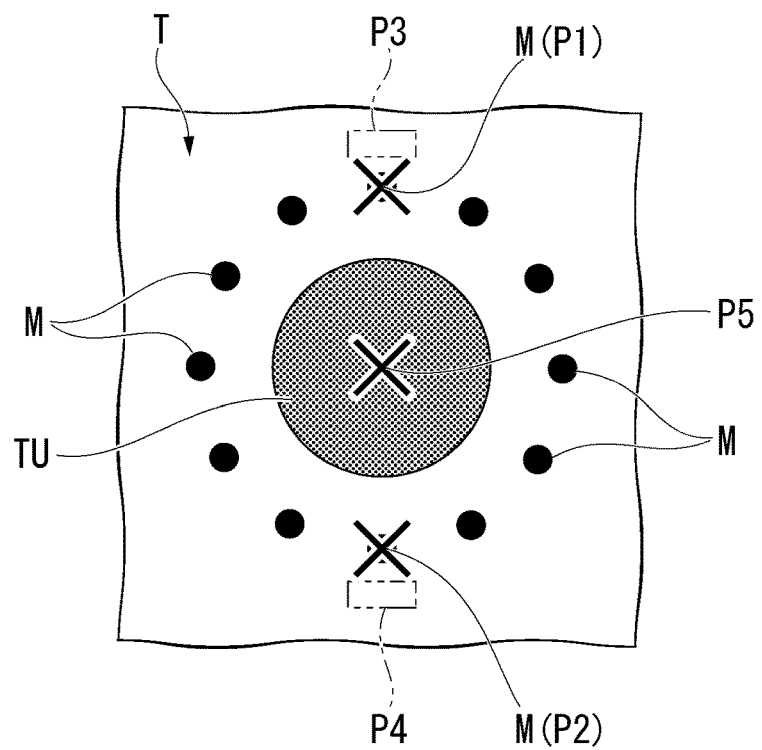
FIG. 35 is a view showing an assistance position in the assistance grasping step.

In the case in which the clip with suture thread R is used as the treatment device for retraction assistance (fourth treatment device), as shown in FIG. 35, the assistance position P5 may be at the position near the line L connection the first position P1 and the second position P2. The reason is that when the grasping forceps GD is moved from the first position P1 to the second position P2, compared with the grasping forceps GD, the clip with suture thread R is difficult to become the obstacle.

Figure 36:
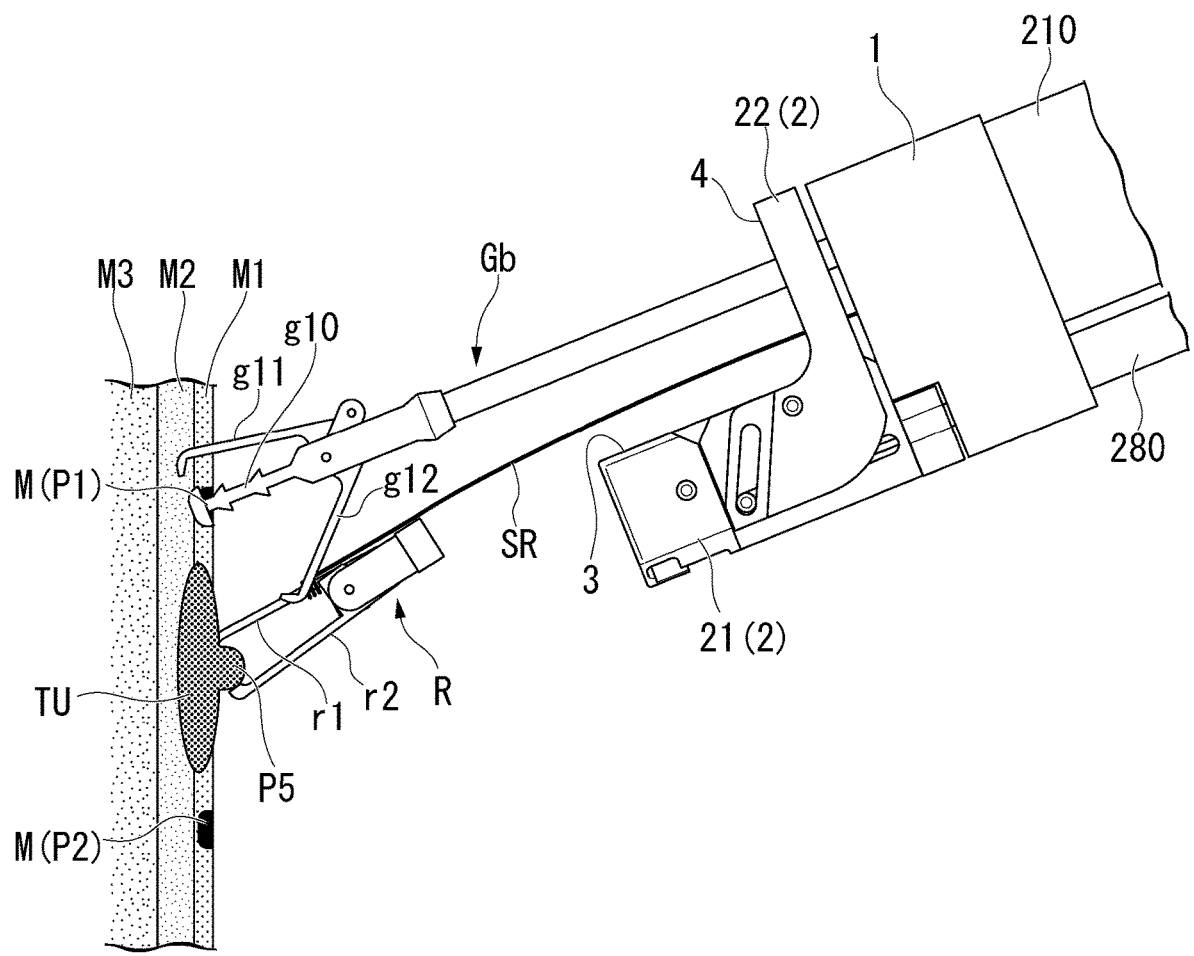
FIG. 36 is a view showing a modification of the first arrangement step and the first grasping step in the present suture method.
Figure 37:
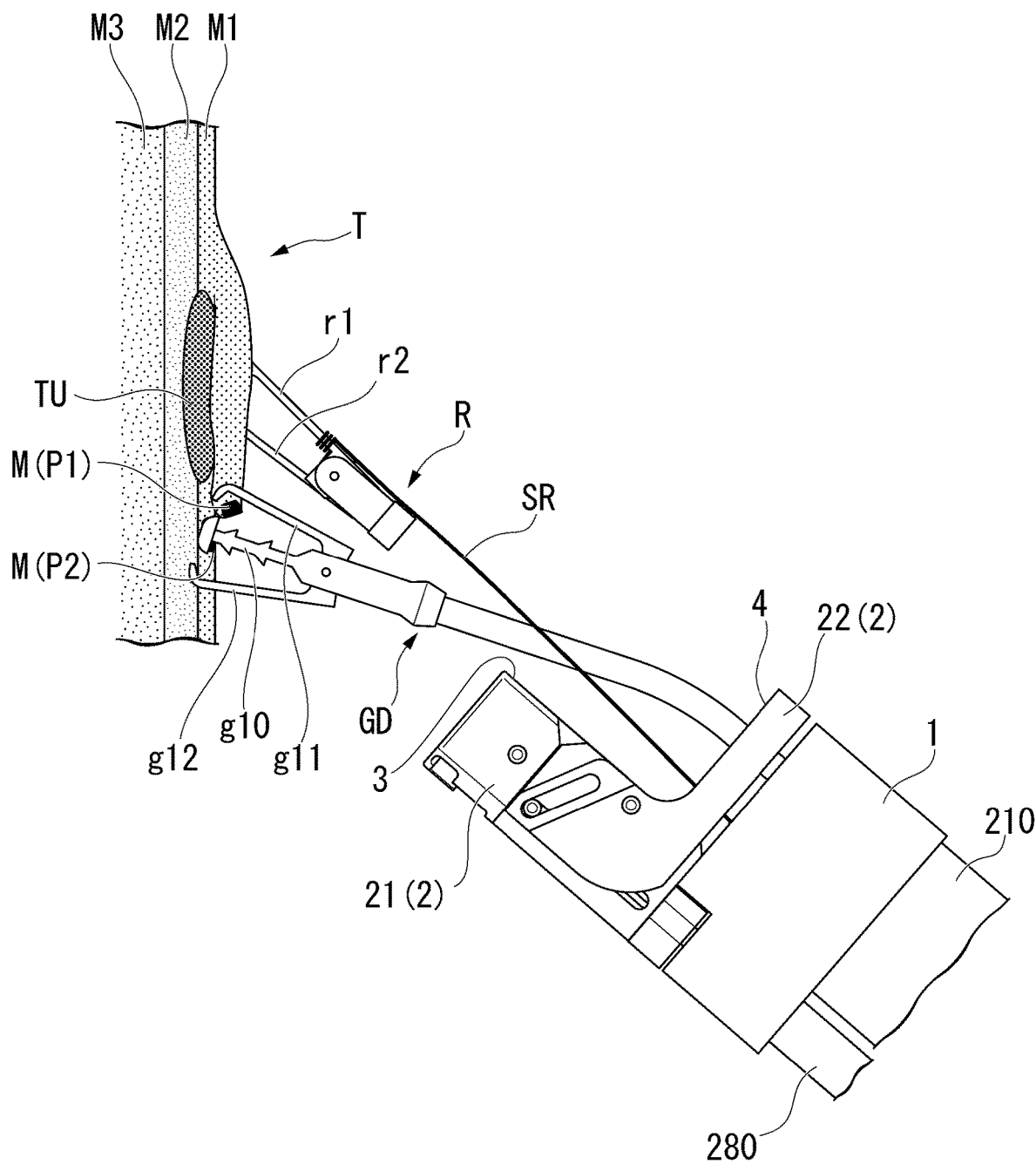
FIG. 37 is a view showing a modification of the second arrangement step and the second grasping step in the present suture method.

As shown in FIG. 36, the surgeon performs the first arrangement step and the first grasping step similarly to the third embodiment. As shown in FIG. 37, the surgeon performs the second arrangement step and the second grasping step similarly to the third embodiment. Next, the surgeon pulls back the grasping forceps GD toward the proximal end side while pulling back the thread SR of the clip with suture thread R grasping the assistance position P5 toward the proximal end side. The surgeon retracts the grasping forceps GD and the clip with suture thread R so as to make the distal end of the grasping forceps GD and the distal end of the clip with suture thread R to be disposed at the more proximal end side of the staple extraction portion 3.

In the case in which the clip with suture thread R is used as the treatment device for retraction assistance (fourth treatment device), both the thread SR of the clip with suture thread R and the grasping forceps GD may pass through the treatment device channel 230 such that the endoscope 200 only has to include a single treatment device channel 230.

Modification 3-2

Figure 38:
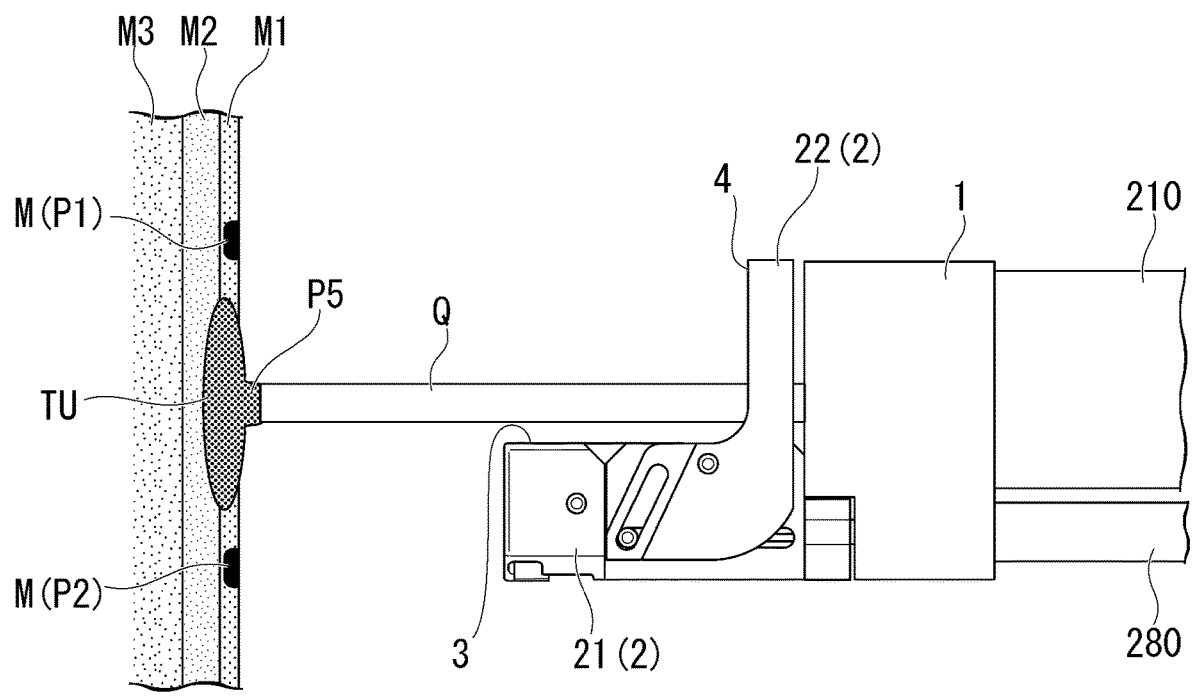
FIG. 38 is a view showing another modification of the assistance grasping step in the present suture method.

In the above-described embodiment, the grasping forceps G is used as the treatment device for retraction assistance (fourth treatment device). However, as shown in FIG. 38, the treatment device for retraction assistance (fourth treatment device) may be a suction tube Q. In the grasping assistance step, the surgeon suctions the assistance position P5 by using the suction tube Q.

Figure 39:
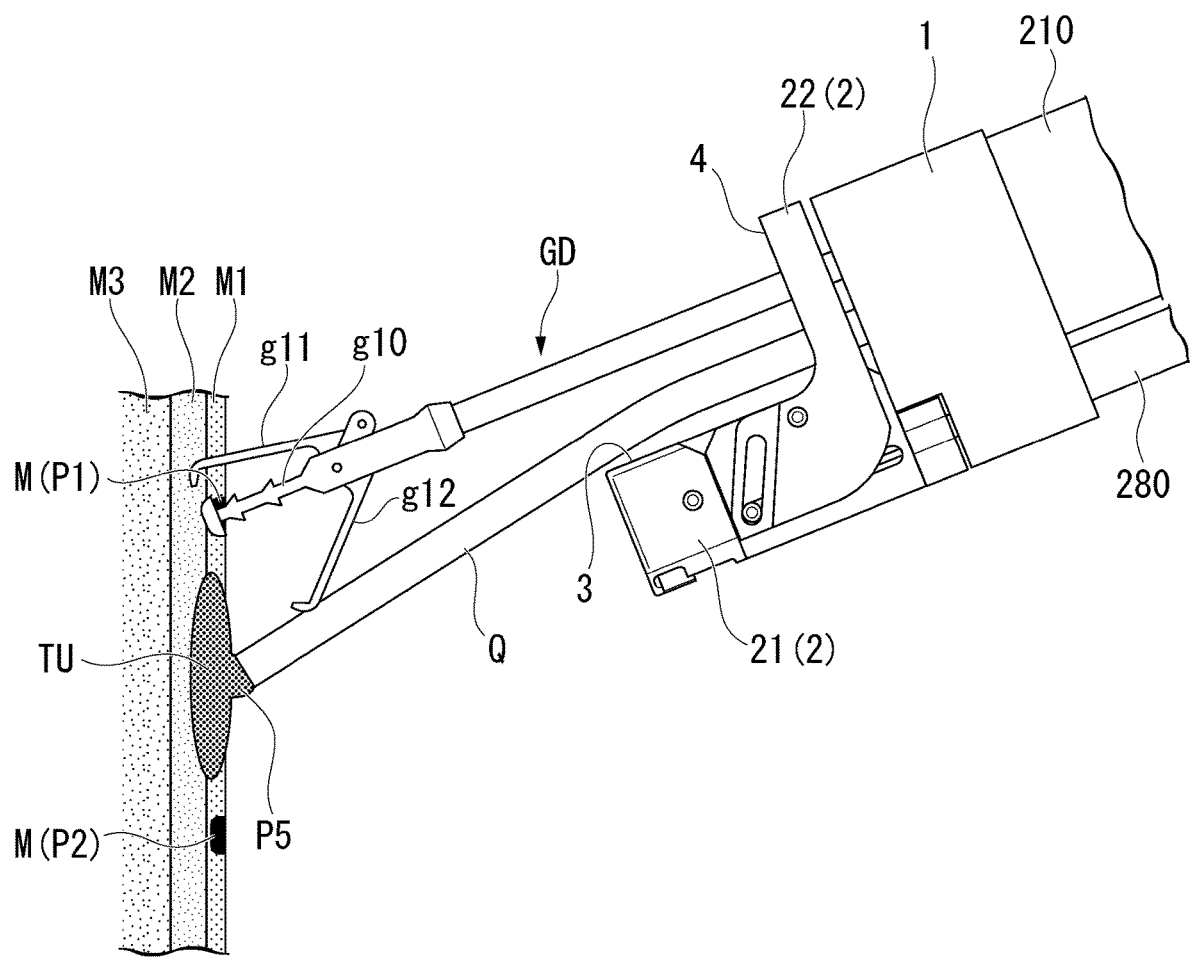
FIG. 39 is a view showing another modification of the first arrangement step and the first grasping step in the present suture method.
Figure 40:
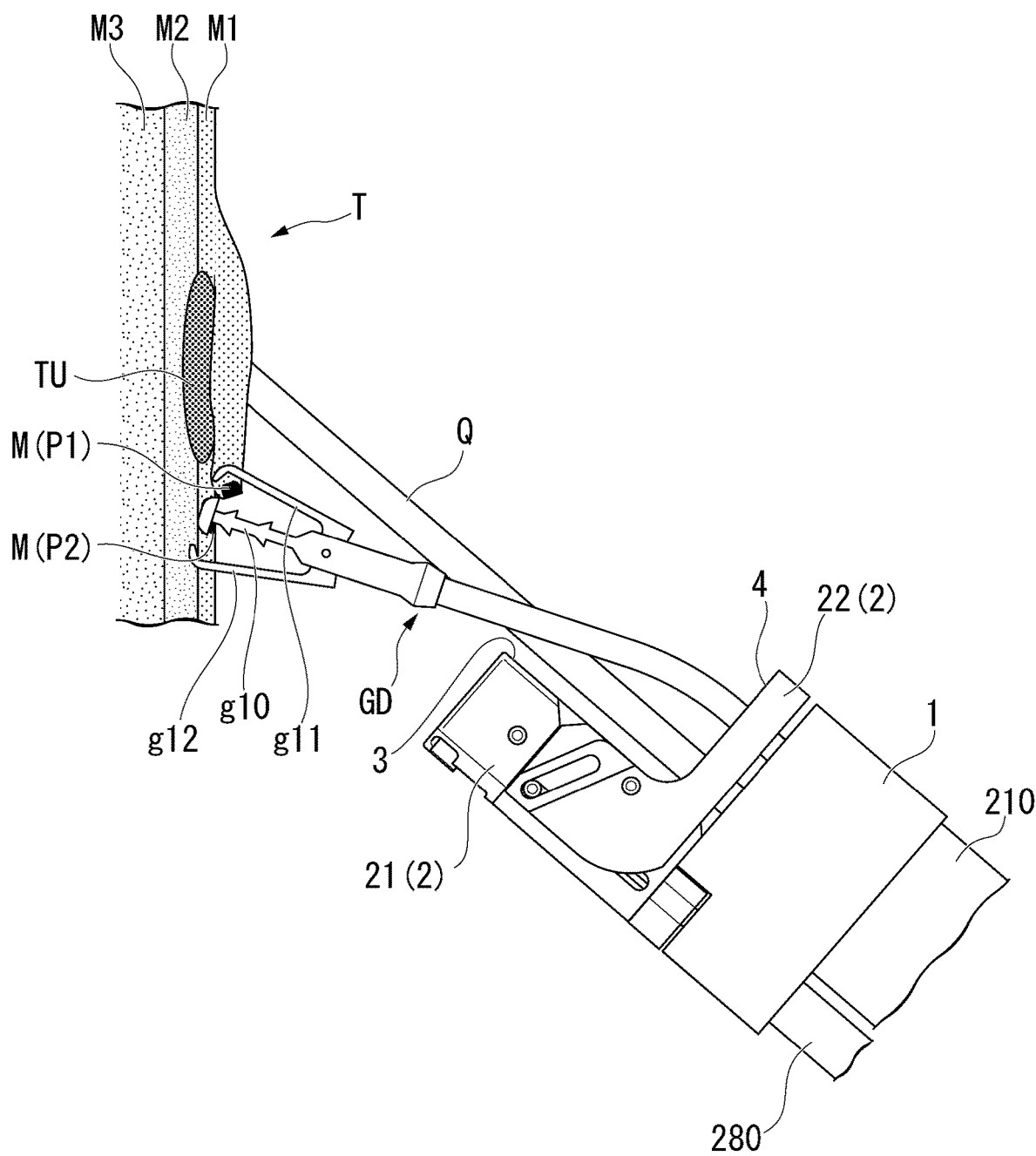
FIG. 40 is a view showing another modification of the second arrangement step and the second grasping step in the present suture method.

As shown in FIG. 39, the surgeon performs the first arrangement step and the first grasping step similarly to the third embodiment. As shown in FIG. 40, the surgeon performs the second arrangement step and the second grasping step similarly to the third embodiment. Next, the surgeon pulls back the grasping forceps GD toward the proximal end side while pulling back the suction tube Q suctioning the assistance position P5 toward the proximal end side. The surgeon retracts the grasping forceps GD and the suction tube Q so as to make the distal end of the grasping forceps GD and the distal end of the suction tube Q to be disposed at the more proximal end side of the staple extraction portion 3.

Modification 3-3

In the above-described embodiment, two treatment devices, that is, the treatment device for retraction (first treatment device) and the treatment device for retraction assistance (fourth treatment device) are used in the retraction step. However, the aspect of the treatment device being used is not limited thereto. For example, three treatment devices may be used in the retraction step or the like. For example, the example of using three grasping forceps G is shown below.

Figure 41:
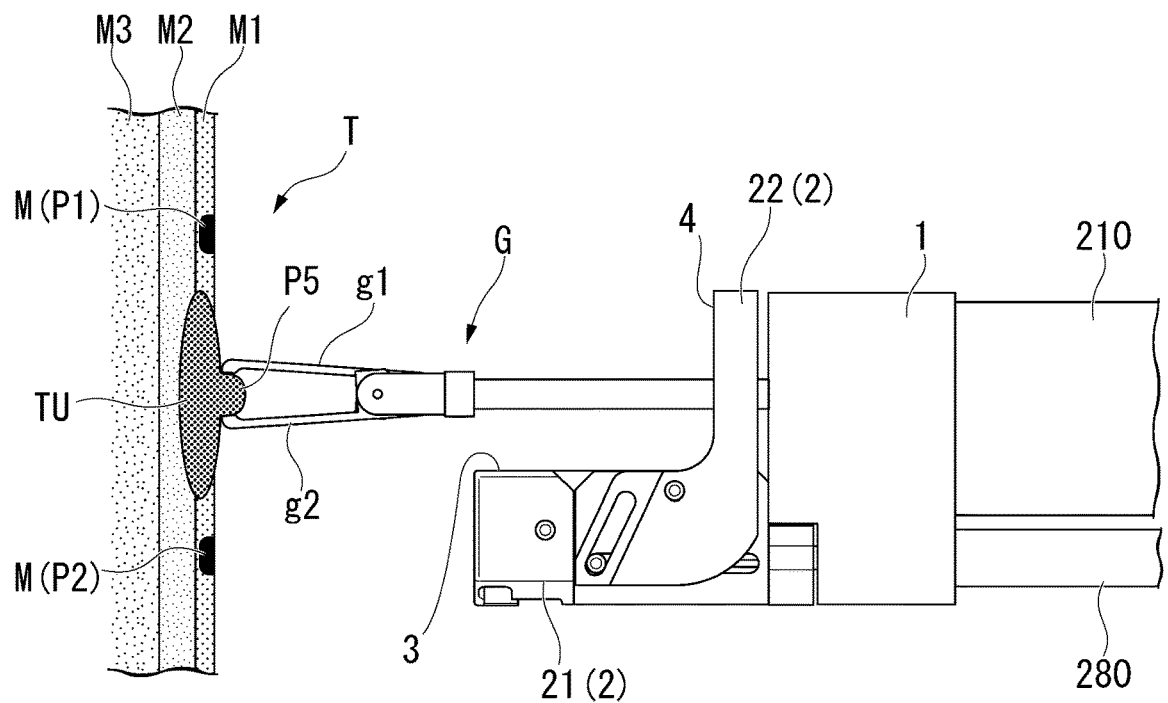
FIG. 41 is a view showing another modification of the assistance grasping step in the present suture method.
Figure 42:
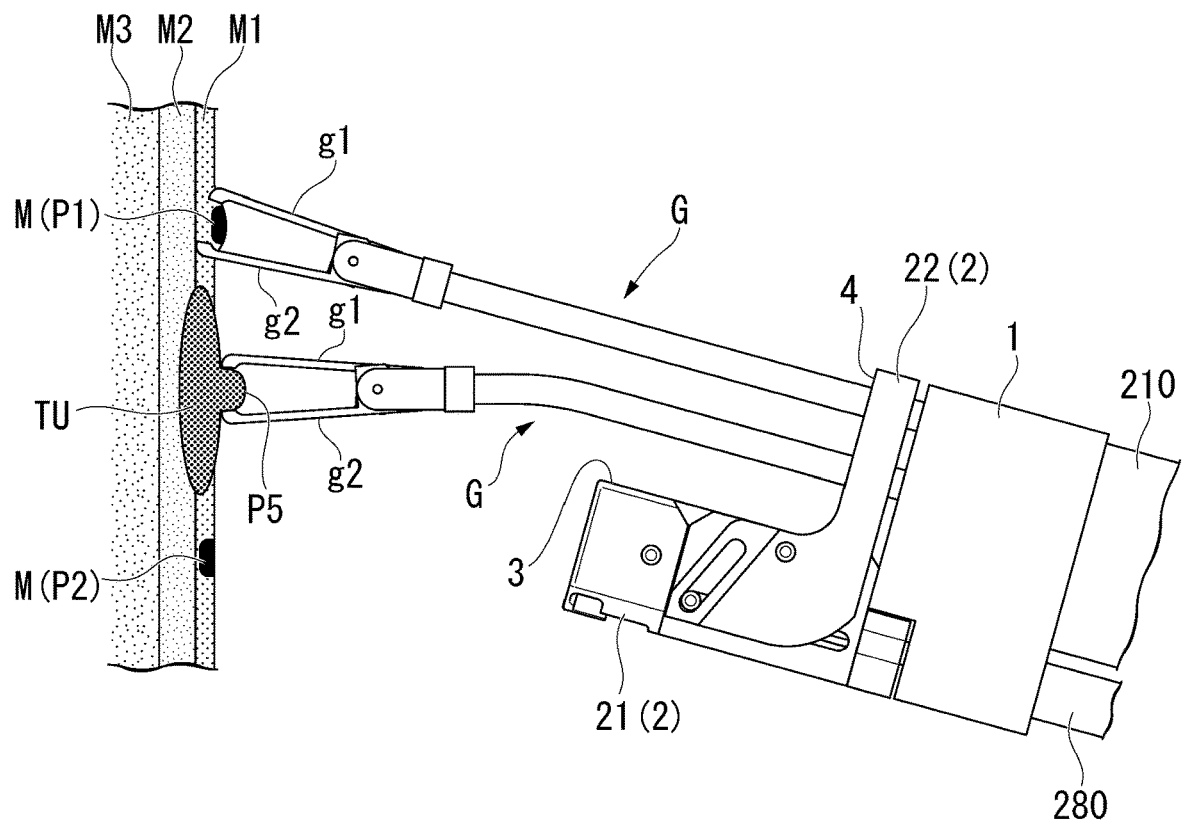
FIG. 42 is a view showing another modification of the first grasping step in the present suture method.
Figure 43:
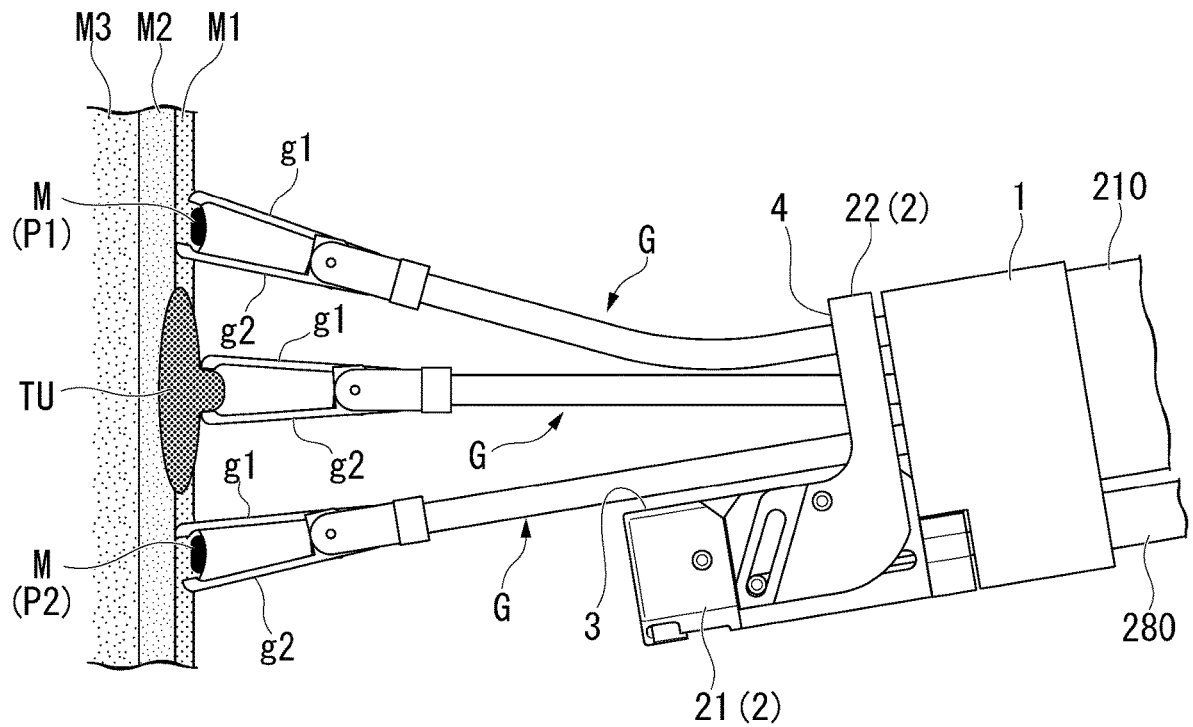
FIG. 43 is a view showing another modification of the second grasping step in the present suture method.

As shown in FIG. 41, the surgeon grasps the assistance position P5 of the tumor TU using the first grasping piece g1 and the second grasping piece g2 of the first grasping forceps G (grasping assistance step). As shown in FIG. 42, the surgeon grasps the first position P1 by the first grasping piece g1 and the second grasping piece g2 of the second grasping forceps G (first grasping step). As shown in FIG. 43, the surgeon grasps the second position P2 by the first grasping piece g1 and the second grasping piece g2 of the third grasping forceps G (second grasping step). The sequence for performing the grasping assistance step, the first grasping step, and the second grasping step is not particularly limited.

The surgeon may definitely retract the whole tumor TU by the medical stapler 100 by using the three grasping forceps G. However, it is necessary for the endoscope to include three treatment device channels 230 to use three grasping forceps G.

Modification 3-4

In the above-described embodiment, two of treatment devices, that is, the treatment device for retraction (first treatment device) and the treatment device for retraction assistance (fourth treatment device) are used in the retraction step. However, the aspect of the treatment device being used is not limited thereto. For example, three treatment devices may be used in the retraction step or the like. For example, the example of using three clips with suture thread R is shown below.

Figure 44:
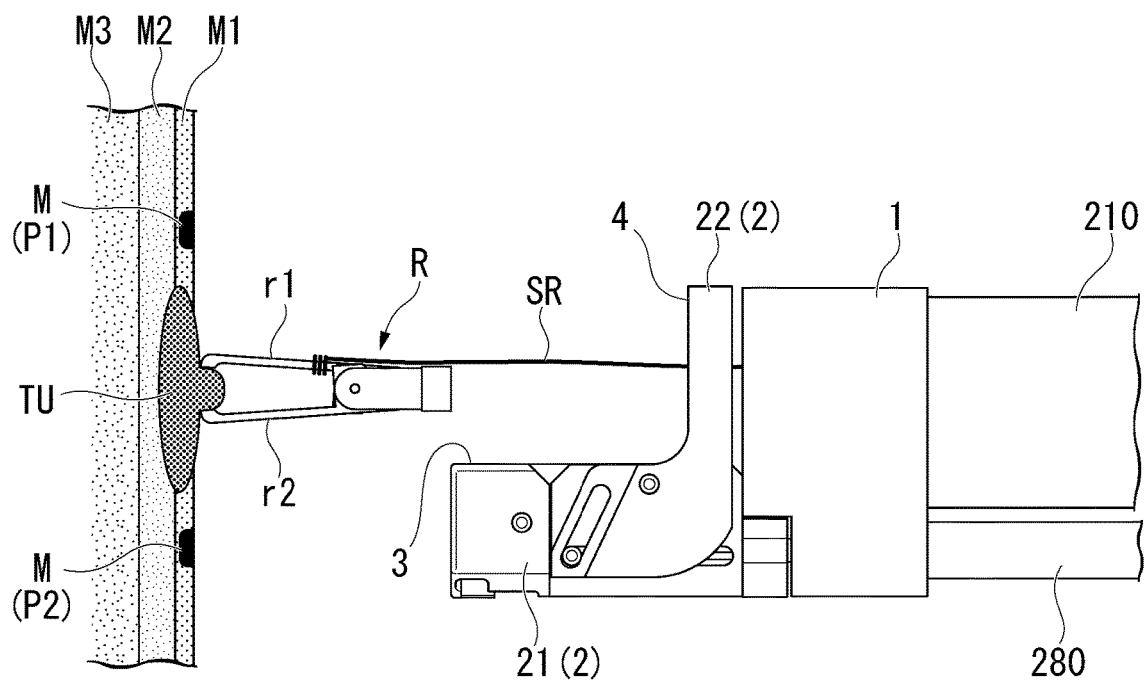
FIG. 44 is a view showing another modification of the assistance grasping step in the present suture method.
Figure 45:
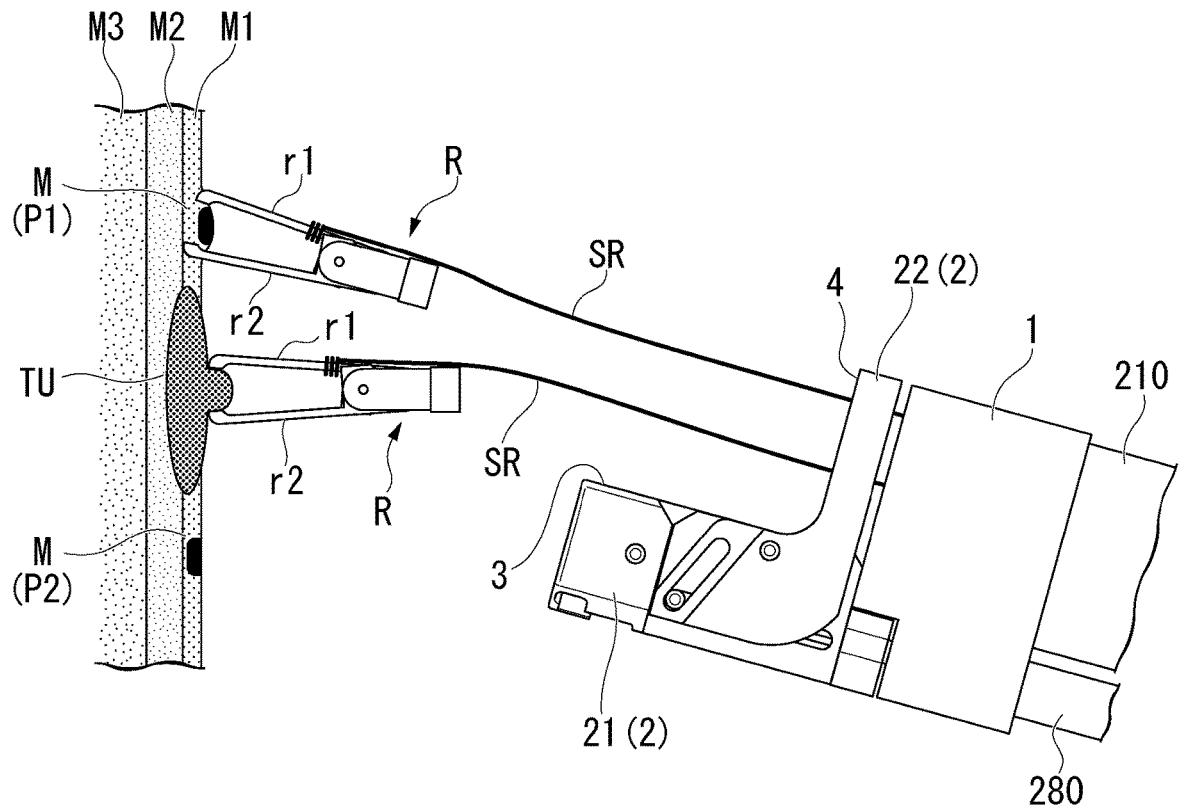
FIG. 45 is a view showing another modification of the first grasping step in the present suture method.
Figure 46:
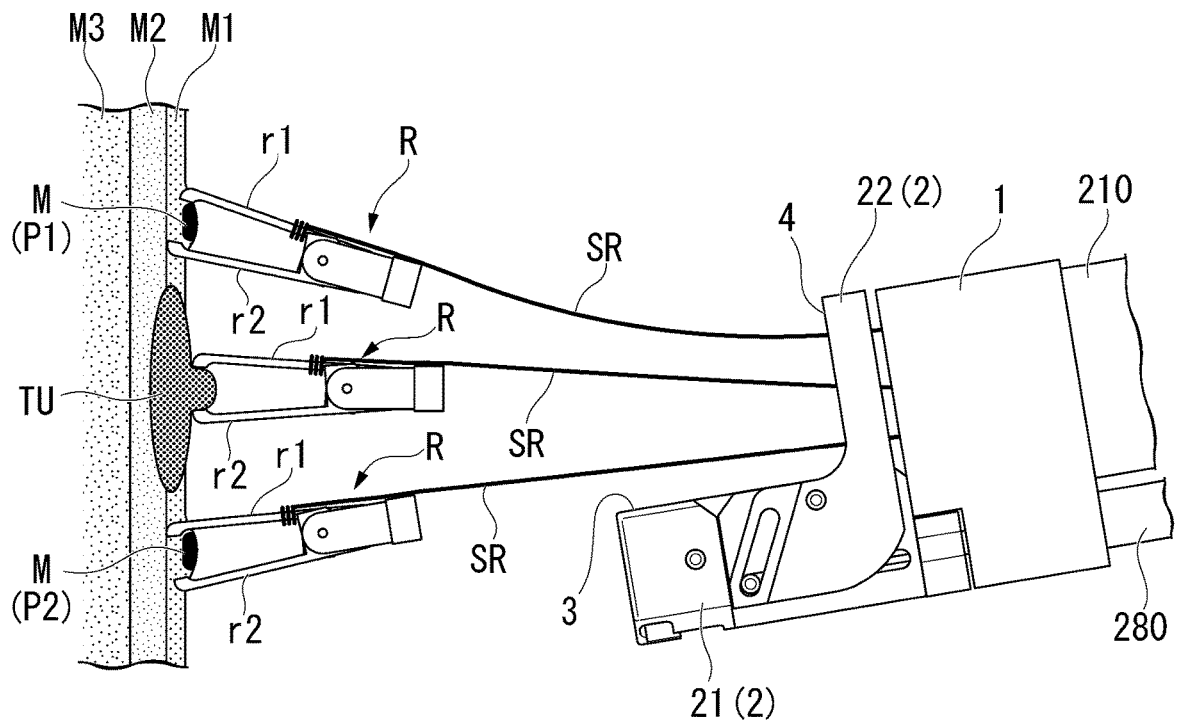
FIG. 46 is a view showing another modification of the second grasping step in the present suture method.

As shown in FIG. 44, the surgeon grasps the assistance position P5 of the tumor TU using the first grasping piece r1 and the second grasping piece r2 of the first clip with suture thread R (grasping assistance step). As shown in FIG. 45, the surgeon grasps the first position P1 by the first grasping piece r1 and the second grasping piece r2 of the second clip with suture thread R (first grasping step). As shown in FIG.

46, the surgeon grasps the second position P2 by the first grasping piece r1 and the second grasping piece r2 of the third clip with suture thread R (second grasping step). The sequence for performing the grasping assistance step, the first grasping step, and the second grasping step is not particularly limited.

The surgeon may definitely retract the whole tumor TU by the medical stapler 100 by using the three clips with suture thread R. Since the three suture thread SR can pass through the treatment device channel 230 together, the endoscope 200 only has to include a single treatment device channel 230.

Modification 3-5

In the above-described embodiment, the medical stapler 100 is used at the suture device. However, the aspect of the suture device is not limited thereto. The suture device using the suture thread and the needle may be used in the suture method according to the above-described embodiment.

What is claimed is:

1. A suture method for suturing peripheral tissues of a lesion site, the method comprising:
    cauterizing the peripheral tissues of the lesion site to form a first marking and a second marking, the first marking and the second marking being positioned opposite to each other across an entirety of the lesion site;
    putting a first grasping piece of a forceps in the first marking;
    putting a second grasping piece of the forceps in the second marking;
    grasping the entirety of the lesion site by the first grasping piece and the second grasping piece while the entirety of the lesion site is between the first grasping piece and the second grasping piece;
    retracting the forceps toward a proximal direction of the forceps while the entirety of the lesion site is grasped between the first grasping piece and the second grasping piece; and
    suturing a first suturing position of the peripheral tissues of the lesion site at an external side of the first marking and the second marking relative to the lesion site in a radial direction.

2. The suture method according to claim 1, further comprising:
    positioning the forceps such that the lesion site is aligned with a longitudinal axis of the forceps.

3. The suture method according to claim 1, further comprising:
    cauterizing the peripheral tissues of the lesion site to form a third marking, wherein the third marking is positioned external to the first grasping piece and the second grasping piece when the first grasping piece is put in the first marking and the second grasping piece is put in the second marking.

4. The suture method according to claim 3, wherein the first marking and the second marking are formed deeper than the third marking in a depth direction of the lesion site.

5. The suture method according to claim 4, wherein the first marking and the second marking are formed by cauterizing a mucosal layer and a submucosa layer of the peripheral tissues of the lesion site.

6. The suture method according to claim 3, wherein the first marking and the second marking are longer than the third marking in a width direction of the lesion site.

7. The suture method according to claim 1, wherein at least one of the first marking and the second marking is formed along a direction that is inclined with respect to a surface of the peripheral tissues of the lesion site such that a depth of the marking from the surface increases toward the lesion site.

8. The suture method according to claim 1, wherein at least one of the first marking and the second marking is formed along a direction that is inclined with respect to a surface of the peripheral tissues of the lesion site such that a depth of the marking from the surface decreases toward the lesion site.

9. The suture method according to claim 1, wherein the suturing of the first suturing position is performed by a medical stapler.

10. The suture method according to claim 1, wherein the peripheral tissues of the lesion site are located at an outside of the lesion site.

* * * * *